(12) United States Patent
Chen et al.

(10) Patent No.: US 7,355,023 B2
(45) Date of Patent: Apr. 8, 2008

(54) ISOLATED NUCLEIC ACIDS AND POLYPEPTIDES ASSOCIATED WITH GLUCOSE HOMEOSTASIS DISORDERS AND METHOD OF DETECTING THE SAME

(75) Inventors: Y. T. Chen, Chapel Hill, NC (US); Alison J. McVie-Wylie, Brookline, MA (US)

(73) Assignee: Duke University, Durham, NC (US)

( * ) Notice: Subject to any disclaimer, the term of this patent is extended or adjusted under 35 U.S.C. 154(b) by 622 days.

(21) Appl. No.: 10/328,198

(22) Filed: Dec. 23, 2002

(65) Prior Publication Data

US 2003/0157075 A1  Aug. 21, 2003

Related U.S. Application Data

(63) Continuation of application No. PCT/US01/20167, filed on Jun. 25, 2001.

(60) Provisional application No. 60/215,477, filed on Jun. 29, 2000.

(51) Int. Cl.
*C07H 21/04* (2006.01)
*C12N 15/63* (2006.01)
*A61K 31/70* (2006.01)
*C12Q 1/68* (2006.01)

(52) U.S. Cl. .................. 536/23.5; 435/320.1

(58) Field of Classification Search ............ None
See application file for complete search history.

(56) References Cited

U.S. PATENT DOCUMENTS 6,639,063 B1 * 10/2003 Edwards et al. ........... 536/23.5
6,849,728 B1 * 2/2005 Bowden et al. ............ 536/23.5
2004/0053258 A1 * 3/2004 Raumann et al. ............ 435/6

FOREIGN PATENT DOCUMENTS

WO  WO 01/75067 A2 * 10/2001

OTHER PUBLICATIONS

Dawson et al., Sequence and functional analysis of GLUT10: A glucose transporter in the type 2 diabetes-linked region of chromosome 20q12-13.1. Mol. Gen. Met. 74:186-199, 2001.*

Adams et al. GenBank Accession No. AQ037826, Jul. 11, 1998.*

Stavrides et al., *Novel human gene mapping to chromosome 20, similar to membrane transporter,* GenBank Accession No. HS28H201 (Nov. 2000).

Branch, *A good antisense molecule is hard to find,* TIBS 23:45-50 (Feb. 1998).

McVie-Wylie et al., *Molecular Cloning of a Novel Member of the GLUT Family of Transporters, SLC2A10 (GLUT 10), Localized on Chromosome 20q13.1: A Candidate Gene for NIDDM Susceptibility,* Genomics 72:13-117 (2001).

Fossey et al., *Homo sapiens glucose transporter (GLUT10) mRNA, complete cds,* GenBank Accession No. AF248053 (Apr. 2001).

Price et al., *A Physical Map of the 20q12-113.1 Region Associated with Type 2 Diabetes,* Genomics 62:208-215 (1999).

Ghosh et al., *Type 2 diabetes: Evidence for linkage on chromosome 20 in 716 Finnish affected sib pairs,* Proc. Natl. Acad. Sci. USA 96:2198-2203 (Mar. 1999).

Mullins and Mullins, *Perspectives Series: Molecular Medicine in Genetically Engineered Animals,* J. Clin. Invest. 98(11) Suppl.:S37-S40 (1996).

Verma et al., *Gene Therapy—promises, problems and prospects,* Nature 389:239242 (Sep. 18, 1997).

Coucke et al. *Mutations in the facilitative glucose transporter GLUT10 alter angiogenesis and cause arterial tortuosity syndrome* Nature Genetics vol. 38, No. 4, (2006), pp. 452-457.

* cited by examiner

*Primary Examiner*—Quang Nguyen
(74) *Attorney, Agent, or Firm*—Jenkins, Wilson, Taylor & Hunt, P.A.

(57) ABSTRACT

An isolated and substantially pure nucleic acid sequence located between D20S119 and D20S178 on human chromosome 20q13, the nucleic acid sequence including: a nucleic acid sequence coding for a glucose transporting protein and having the sequence shown in SEQ ID NO: 1; or a nucleic acid sequence having at least 70% sequence identity with the nucleic acid sequence shown in SEQ ID NO: 1. The disclosed nucleic acid sequences map to a locus associated with human Type II diabetes mellitus and, therefore, therapeutic and diagnostic screening methods, which accommodate naturally and artificially occurring polymorphisms, are also disclosed.

5 Claims, 8 Drawing Sheets

```
CTCAAAACATGGCAGCTCAATTGCTTCATCAGAGCAAACAAGTGAGAGATCTCGAAACTGA
ACAACACAGAAATCATTTATAACCTAATCCGAAAATGACATCCACCATATTTGCCGTCTTC
TATTCATTAGACGTTGCTAAGTGATACTTCTAGTGACATCTAGAAGAGAAGAGGATGCCAC
TAGGCCACGAATACCAGGAGGGTCTCAGTGTAATCAGACTTTTTATATGAAGGCTCAGGGA
TCCAGGCACCAGTATTCCAGTGACCCAGCCTCAGAAGTTACACAGTGTCACTCTGCAGGCT
ACTGATCAAACCAGTCACAAGCCCACTTTTATTTCAAGGGAAGGAACAACGAATTCTGGAG
CCATGTTTTCAAACTGCCCCAGCTATTATTATTTTTGAAACTGTGCAAGGATCCCCTGGTT
CAGAGGTCTTATGGATGCTGTCATCTTTGCTGAGATACCTGCTTGTGCCTTCAGCATGGAA
GAATGCCTGTGTATCCACCTGTACGGTAGGGGTCGCTGTGACTTTGACTGGTGAGGGTACA
GCCACTGGTGCACATGCAAAGGTGCCTATCTGTGAACACGTATTGAGAGGCTGGATAAGGC
TGCGCCCATGTGAGTGCTGGGCTTGTACGTGCATTTTTGCCTGAGTGAGCATTAGTGGCAG
TGTCCCCAGCCTACCCCTTTCCTGAATCCCAGGCTCATAGCCAACTGCCCACCTATTTCCA
CGTGGATGCCTGCTGAGCACCTCAAATGTCACACAGCCAAGACAGAACTCTGGATCTCCTT
TCCCAGCCACAAGCTGCCCCTCTTCCAGTCTGTAAGTTCTTACGGAGCATATATATGTGAT
CTGCCTACTTTTCTCCAACCTCACCACAGTGACATGAGCCCAAACCAACTTCTCACCTTGC
AACAGCCTCCCAGGTGGGAAGGCTGAGTATTCTGGCCCTTAACCAGTTAGAACTCCCCAGT
TATCTGTCCTGCTGATGGGGTTGAAATCTACATTCCTGACCCTGGCCCACCAAAGCCCCTC
CCTTAGCTCCCATCTCCCTCCTCTCTCCCTGTCTTCTCCTCTGCTCCAGACACTCTGGCTT
CATTTCTGCGTTTTTTGTACCCCATAAGCTCCTTCCCACCCCGGGGCCTTTGCCTTTGCTG
TTCCCCCTGCGGGGAATGCCGGATCTCTGCTCAGATATCCTCTTCTCAGATCAGCAAGCTA
AAGCAGCCACCTGTGTCTGCCTAACCCACCACCGTAGTTTAACTTTCTGCCTAGTCTTTAT
CACTAGCTGATATTTCTCAGGATCCTTTAGTTACTTCTTTTTCGTCTTCCCCTCCTAGAAT
GTAAACTCTTCCCCTCCTAGAAGGTAAACAAAAGACCTGTTCTGTTTTGTTCTTCGGCCCA
TCCCAAGCCTAGCGTAGTGCCTGGTATGTGGTGGTGTCCAAACCCAAGCGTGGAGTGAATG
AGGGATGAATCCATGAGAGAGTGAGCGGCTCCAGTGGGTATGCGCGAGTGTCTCACTCGGT
GTAGATGTGTGTGTTGTGTGTGTTGTGTGTGTGCGCACGCTGGGGAGGCCAGACAAGTGTG
GACCAGTGATTGGGGCACCTCTTCCCTGCAAAGAGGCCAGGGAAGACAGTGCGTGTGGGG
TCTTCTACCAGGGAGGATGGCTTGCTGGTGTGTCCCCCCAGGGGAGGACTACCAACGAAG
GGGACCCGGGAGATGGCGGGTGGGGCCCCGGGAGGACAGTGGGCGAGGGAGGGGGTCCT
TGCCAGGCCTGGGCGGCCGGGGCGGTCCTGGCTCCCCTCCGTCCCGCCTCCAGGCCTC
GGGGCCTGGCTGGCCGACGTGGCGTTGGCGGCGCTGCGCGCGGGAGGGCAGGGCAGGAGGG
ACAGAGGCGGGGCGGGCCGGAAAGTTTGTCCGGCGGCAGCGGCGTTGGGGACTCCGGCGG
GGGATGCGCGCCCGGCCCCTCAGCGCCCCAGCACGCCGCCGAGTCCCGCTCGCC
```

FIG. 1(A)

```
      Met Gly His Ser Pro Pro Val Leu Pro Leu Cys Ala Ser Val Ser
  1   ATG GGC CAC TCC CCA CCT GTC CTG CCT TTG TGT GCC TCT GTG TCT    45

Leu Leu Gly Gly Leu Thr Phe Gly Tyr Glu Leu Ala Val Ile Ser
 46   TTG CTG GGT GGC CTG ACC TTT GGT TAT GAA CTG GCA GTC ATA TCA    90

Gly Ala Leu Leu Pro Leu Gln Leu Asp Phe Gly Leu Ser Cys Leu
 91   GGT GCC CTG CTG CCA CTG CAG CTT GAC TTT GGG CTA AGC TGC TTG   135

Glu Gln Glu Phe Leu Val Gly Ser Leu Leu Leu Gly Ala Leu Leu
136   GAG CAG GAG TTC CTG GTG GGC AGC CTG CTC CTG GGG GCT CTC CTC   180

Ala Ser Leu Val Gly Gly Phe Leu Ile Asp Cys Tyr Gly Arg Lys
181   GCC TCC CTG GTT GGT GGC TTC CTC ATT GAC TGC TAT GGC AGG AAG   225

Gln Ala Ile Leu Gly Ser Asn Leu Val Leu Leu Ala Gly Ser Leu
226   CAA GCC ATC CTC GGG AGC AAC TTG GTG CTG CTG GCA GGC AGC CTG   270

Thr Leu Gly Leu Ala Gly Ser Leu Ala Trp Leu Val Leu Gly Arg
271   ACC CTG GGC CTG GCT GGT TCC CTG GCC TGG CTG GTC CTG GGC CGC   315

Ala Val Val Gly Phe Ala Ile Ser Leu Ser Ser Met Ala Cys Cys
316   GCT GTG GTT GGC TTC GCC ATT TCC CTC TCC TCC ATG GCT TGC TGT   360

Ile Tyr Val Ser Glu Leu Val Gly Pro Arg Gln Arg Gly Val Leu
361   ATC TAC GTG TCA GAG CTG GTG GGG CCA CGG CAG CGG GGA GTG CTG   405

Val Ser Leu Tyr Glu Ala Gly Ile Thr Val Gly Ile Leu Leu Ser
406   GTG TCC CTC TAT GAG GCA GGC ATC ACC GTG GGC ATC CTG CTC TCC   450

Tyr Ala Leu Asn Tyr Ala Leu Ala Gly Thr Pro Trp Gly Trp Arg
451   TAT GCC CTC AAC TAT GCA CTG GCT GGT ACC CCC TGG GGA TGG AGG   495

His Met Phe Gly Trp Ala Thr Ala Pro Ala Val Leu Gln Ser Leu
496   CAC ATG TTC GGC TGG GCC ACT GCA CCT GCT GTC CTG CAA TCC CTC   540

Ser Leu Leu Phe Leu Pro Ala Gly Thr Asp Glu Thr Ala Thr His
541   AGC CTC CTC TTC CTC CCT GCT GGT ACA GAT GAG ACT GCA ACA CAC   585

Lys Asp Leu Ile Pro Leu Gln Gly Gly Glu Ala Pro Lys Leu Gly
586   AAG GAC CTC ATC CCA CTC CAG GGA GGT GAG GCC CCC AAG CTG GGC   630

Pro Gly Arg Pro Arg Tyr Ser Phe Leu Asp Leu Phe Arg Ala Arg
631   CCG GGG AGG CCA CGG TAC TCC TTT CTG GAC CTC TTC AGG GCA CGC   675

Asp Asn Met Arg Gly Arg Thr Thr Val Gly Leu Gly Leu Val Leu
676   GAT AAC ATG CGA GGC CGG ACC ACA GTG GGC CTG GGG CTG GTG CTC   720

Phe Gln Gln Leu Thr Gly Gln Pro Asn Val Leu Cys Tyr Ala Ser
721   TTC CAG CAA CTA ACA GGG CAG CCC AAC GTG CTG TGC TAT GCC TCC   765

Thr Ile Phe Ser Ser Val Gly Phe His Gly Gly Ser Ser Ala Val
766   ACC ATC TTC AGC TCC GTT GGT TTC CAT GGG GGA TCC TCA GCC GTG   810

Leu Ala Ser Val Gly Leu Gly Ala Val Lys Val Ala Ala Thr Leu
811   CTG GCC TCT GTG GGG CTT GGC GCA GTG AAG GTG GCA GCT ACC CTG   855

Thr Ala Met Gly Leu Val Asp Arg Ala Gly Arg Arg Ala Leu Leu
856   ACC GCC ATG GGG CTG GTG GAC CGT GCA GGC CGC AGG GCT CTG TTG   900

Leu Ala Gly Cys Ala Leu Met Ala Leu Ser Val Ser Gly Ile Gly
901   CTA GCT GGC TGT GCC CTC ATG GCC CTG TCC GTC AGT GGC ATA GGC   945
```

FIG. 1(B)

```
        Leu Val Ser Phe Ala Val Pro Met Asp Ser Gly Pro Ser Cys Leu
946     CTC GTC AGC TTT GCC GTG CCC ATG GAC TCA GGC CCA AGC TGT CTG     990

Ala Val Pro Asn Ala Thr Gly Gln Thr Gly Leu Pro Gly Asp Ser
991     GCT GTG CCC AAT GCC ACC GGG CAG ACA GGC CTC CCT GGA GAC TCT     1035

Gly Leu Leu Gln Asp Ser Ser Leu Pro Pro Ile Pro Arg Thr Asn
1036    GGC CTG CTG CAG GAC TCC TCT CTA CCT CCC ATT CCA AGG ACC AAT     1080

Glu Asp Gln Arg Glu Pro Ile Leu Ser Thr Ala Lys Lys Thr Lys
1081    GAG GAC CAA AGG GAG CCA ATC TTG TCC ACT GCT AAG AAA ACC AAG     1125

Pro His Pro Arg Ser Gly Asp Pro Ser Ala Pro Pro Arg Leu Ala
1126    CCC CAT CCC AGA TCT GGA GAC CCC TCA GCC CCT CCT CGG CTG GCC     1170

Leu Ser Ser Ala Leu Pro Gly Pro Pro Leu Pro Ala Arg Gly His
1171    CTG AGC TCT GCC CTC CCT GGG CCC CCT CTG CCC GCT CGG GGG CAT     1215

Ala Leu Leu Arg Trp Thr Ala Leu Leu Cys Leu Met Val Phe Val
1216    GCA CTG CTG CGC TGG ACC GCA CTG CTG TGC CTG ATG GTC TTT GTC     1260

Ser Ala Phe Ser Phe Gly Phe Gly Pro Val Thr Trp Leu Val Leu
1261    AGT GCC TTC TCC TTT GGG TTT GGG CCA GTG ACC TGG CTT GTC CTC     1305

Ser Glu Ile Tyr Pro Val Glu Ile Arg Gly Arg Ala Phe Ala Phe
1306    AGC GAG ATC TAC CCT GTG GAG ATA CGA GGA AGA GCC TTC GCC TTC     1350

Cys Asn Ser Phe Asn Trp Ala Ala Asn Leu Phe Ile Ser Leu Ser
1351    TGC AAC AGC TTC AAC TGG GCG GCC AAC CTC TTC ATC AGC CTC TCC     1395

Phe Leu Asp Leu Ile Gly Thr Ile Gly Leu Ser Trp Thr Phe Leu
1396    TTC CTC GAT CTC ATT GGC ACC ATC GGC TTG TCC TGG ACC TTC CTG     1440

Leu Tyr Gly Leu Thr Ala Val Leu Gly Leu Gly Phe Ile Tyr Leu
1441    CTC TAC GGA CTG ACC GCT GTC CTC GGC CTG GGC TTC ATC TAT TTA     1485

Phe Val Pro Glu Thr Lys Gly Gln Ser Leu Ala Glu Ile Asp Gln
1486    TTT GTT CCT GAA ACA AAA GGC CAG TCG TTG GCA GAG ATA GAC CAG     1530

Gln Phe Gln Lys Arg Arg Phe Thr Leu Ser Phe Gly His Arg Gln
1531    CAG TTC CAG AAG AGA CGG TTC ACC CTG AGC TTT GGC CAC AGG CAG     1575

Asn Ser Thr Gly Ile Pro Tyr Ser Arg Ile Glu Ile Ser Ala Ala
1576    AAC TCC ACT GGC ATC CCG TAC AGC CGC ATC GAG ATC TCT GCG GCC     1620

Ser End
1621    TCC TGA
```

FIG. 1(B) (contd)

```
GGTCTTTTGGGAGTGGCCCCTGCCCCCAAAGGTGGTCTGCTTTTGCTGGGGTA
AAAAGGATGAAAGTCTGAGAATGCCCAACTCTTCATTTTGAGTCTCAGGCCCTGA
AGGTTCCTGAGGATCTAGCTTCATGCCTCAGTTTCCCCATTGACTTGCACATCTC
TGCAGTATTTATAAGAAGAATATTCTATGAAGTCTTTGTTGCACCATGGACTTTTC
TCAAAGAATCTCAAGGGTACCAATCCTGGCAGGAAGTCTCTCCCGATATCACCC
CTAAATCCAAATGAGGATATCATCTTTTCTAATCTCTTTTTTCAACTGGCTGGGAC
ATTTTCGGAAGGGGGAAGTCTCTTTTTTTACTCTTATCATTTTTTTTTTTGAGGT
GGAGTCTCATTCTGTTGCCCAGGCTGGCCTGATCTTGGCTCACTGCAACCTCCA
CCTCCTGAGTTCAAGCGATTCTTGTGCCTCAGCCTCCTAAGCAGCTGGGACTAC
AGGCGCATGCAACCATACCCAGCTAATTTATTTTTAGCAGAGATGGGGTTTCACT
GTGTTGGCCAGGCTGGTCGTGAACTCCTGAGCTCAAGTGATCCACCCACCTCA
GCCTCCCAGAGTGCTAGGATTACAGGCCTTTTGACTCTTTTATCTGAGTTTTATT
GACCCCTCTAATTCTCTTACCCAGAATATTTATCCTTCACCAGCAACTCTGACTCT
TTGACGGGAGGCCTCAGTTCTAGTCCTTGGTCTGCTGGTGTCATTGCTGTAGGA
ATGACCACGGGCCTCAGTTTCCCCATTTGTATAATGGGAAGCCTGTACCAGGTC
ATTCTTAAGATTTCTCCTGACTCCAGTGAGCTGGAATTCTAAATGCTGGTCTAGG
AGCTGTCTCCAGGATGGTGCAGGATGGCTTTGCGGAAAGGAGATGGGTTTGGA
GGCCAACAAACCTGCTTGTCAATATTGCCTTTGCCTCTTGGCAGCCCTTGAACTT
GAGTAAATAACAACTCCCTGAACCTCAGTTTCCTCATCTGCAGAATGGGGATAAT
TATGTCCCAGGGGTATATTTAGACCCTGTTTCCTTTCAGGAGGGTCCCCAGCTG
GTCCAGGGCCTGGGAAATTTCTACTTATCCTCATTACCCAGGTCCCTCCTTTGGA
CCCTGTAAAGGGTCAGGGTGAATCAGATGGGGGACTGAGCAAGTAGCTATGAC
TGCAGATCATGTAAGGAAGGGACTGACAAGAAGCTCCCAGATGCTGGGGAGAA
TGAAGAGCTAAAATAGATCCTAGGTGCTGGATGCTTTGTCATCCATGCGTGCAC
ATATGGGTGCTGGCAGAGCCCCCAAGGACTCTGGCCTCTCGAGTTCTCCTATCT
TCTCCATTCTAGATGCTTCCCTTGTATCCAGTGATGTGCTGGAGCTGGCTTTGCC
AAGCTTGTGAGAGCTGGTTGCTACATTTTCAGGATTTTTACAAGTTGGTAAACAC
AGCCATTATAAAAAATTAAATGATTTAAATTTATAATTAAGTAAATTACATTAAAAC
AAAAAAATTATACTCAAAATTCATTACTTAATTTTACTACCTGTTACTATTATCTGT
GCTTTTGAGGCTATTTCTACATAGTAACTCTTATGGAGACCTAGGGGAGACACC
GCGCATCTCTTCCTGATTCCCCACTCAATGACATCATGTTAGTCTTTGGTTGCTT
AACTGGCTGTGGGGAGTGTTTTTGTATCACAAAGATTAGAGAGGACTACACATC
AGGGCTTGATTTATTGTTTGTTGATTTTCTAGACTTCAGAACATGCTGGATAAAAT
GTCAGTAATGCAAATTAAACTTTAAAGTATGTCTTGTTTGTAGCCAATACATGGTG
TATAGCACCAAAAAATGGAGGGATTATTCTTCCAGTAGTTGAACACTGTCATCCG
TTTCAGCTGACAGCTGCTCAAATCATTTAAGAAGGAGTTCTGACATTCATTTTCAT
TGTTTTACTTTTGTCTTCCTCACTAGTGTAAACAAAAATTTCAACCAGCATTCATG
CCGAACCTATACCCATTCTTCAGTGCCTAGCTGTACAGTTATCAGGGATTTTTAT
TTGTAGTCTAATTTTGTCAAATCATGGCCAAATCGCAGTGATAGTTGACTTTGGA
TACAAGGTTTGGCAAAAAAAAAATATTAACAAAATATTCTGTAAGAATCAATTGT
CTATATGGAATTTAGGATAAAGAATATTTACAATAAAGAATATTTACAATAAAGAG
TTTATTATTATTTGTAAGTTGTGTGCAACAAACATACCCTTTATCTCTGTAAAATTT
ATACACACAAAAATTAACAAAAGATTCTGTAAGAATTAATTGGCTATATGGAATTT
AGGATAGAATATTTACAATAAAGAGTATTTACAAT
```

FIG. 1(C)

```
                                            <-------TM1------->
humglut1   MEPSSKKLTG R....LMLAV GGAVLGSLQF GYNTGVINAP QKVIEEFYNQ TMVHRYGESI LPTTLTLMS  LSVAIFSVGG MIGSFSVGLF VNRFGRRNSM
newglut    ---------HG HSPPVLPLCA SVSLLGGLTF GYELAVISGA LLPLQ..... ...LDFGLSC LEQ......E FLVGSLLLGA LLASLVGGFL IDCYGRKQAI -------TM3-------->                          <-------TM4-------->                            <-------TM5-------->
humglut1   LMMNLLAFVS AVLMGFSKLG KSFEMLILGR FIIGVYCGLT TGFVPMYVGE VSPTAFRGAL GTLHQLGIVV GILIAQVFGL DSIMGNKDLH PLLLSIFIP
newglut    LGSNLVLLAG SLTLG...LA GSLAWLVLGR AVVGFAISLS SMACCIYVSE LVGPRQRGVL VSLYEAGITV GILLSYALAY .ALAGTPWGW RHMFGHATAP <-------TM7-------->
humglut1   ALLQCIVLPF CPESPRFLLI NRNEENRAKS VLKKLRGTAD VTHDLQEMKE ESRQMMREKK VTILELFRS. PAYRQPILIA VVLQLSQQLS GINAVFYYST
newglut    AVLQSLSLLF LPAG....... ..TDETATHK DLIPLQG... .........GE APKLGPGRPR YSFLDLFRAR DNMRGRTTVG LGLVLFQQLT GQPNVLCYAS <-------TM8-------->                            <-------TM9-------->
humglut1   SIFEKAGV.. .QQPVYATIG SGIVNTAFTV VSLFVVERAG RRTLHLIGLA GMAGCAILMT IALALLFQLP .......... ..........
newglut    TIFSSVGFHG GSSAVLASVG LGAVKVAATL TAMGLVDRAG RRALLLAGCA LMALSVSGIG LVSFAVPMDS GPSCLAVPNA TGQTGLPGDS GLLQDSSLPP <-------TM10-------->                         <-------TM11-------->
humglut1   .......... .......... .......... .......... .HMSYLSIVA IPGFVAPFEV GPGPIPWFIV ABLFSQGPRP AIAVAGFSN
newglut    IPRTNEDQRE PILSTAKKTK PHPRSGDPSA PPRLALSSAL PGPPLPARGH ALLRWTALLC LWVFVSAFSF GFGPVTHLVL SEIYPVEIRG RAFAFCNSFN <-------TM12-------->
humglut1   MTSNPIVGMC FQYVEQLCG. PYVFIIFTVL LVLFFIFTYP KVPETKGRTF DEIASGFRQ. ......GGAS QSDKTPEELF HPLGADSQV*---
newglut    WRANLPISLS FLDLIGTIGL SWTPLLYGLT AVLGLGFIYL FVPETKGQSL AEIDQQFQKR RFTLSFGHRQ NSTGIPYSRI EISAAS*---
```

FIG. 5

SEQUENCE LISTING

```
<160> NUMBER OF SEQ ID NOS: 4

<210> SEQ ID NO 1
<211> LENGTH: 4075
<212> TYPE: DNA
<213> ORGANISM: Homo sapiens
<220> FEATURE:
<221> NAME/KEY: CDS
<222> LOCATION: (53)..(1678)

<400> SEQUENCE: 1
atgcgcgccc ggcccctcag cgcccccagc acgccgccga gtcccgctcg cc atg ggc      58
                                                            Met Gly
                                                             1 cac tcc cca cct gtc ctg cct ttg tgt gcc tct gtg tct ttg ctg ggt     106
His Ser Pro Pro Val Leu Pro Leu Cys Ala Ser Val Ser Leu Leu Gly
  5                  10                  15
```

```
ggc ctg acc ttt ggt tat gaa ctg gca gtc ata tca ggt gcc ctg ctg      154
Gly Leu Thr Phe Gly Tyr Glu Leu Ala Val Ile Ser Gly Ala Leu Leu
     20                  25                  30 cca ctg cag ctt gac ttt ggg cta agc tgc ttg gag cag gag ttc ctg      202
Pro Leu Gln Leu Asp Phe Gly Leu Ser Cys Leu Glu Gln Glu Phe Leu
 35                  40                  45                  50 gtg ggc agc ctg ctc ctg ggg gct ctc ctc gcc tcc ctg gtt ggt ggc      250
Val Gly Ser Leu Leu Leu Gly Ala Leu Leu Ala Ser Leu Val Gly Gly
             55                  60                  65 ttc ctc att gac tgc tat ggc agg aag caa gcc atc ctc ggg agc aac      298
Phe Leu Ile Asp Cys Tyr Gly Arg Lys Gln Ala Ile Leu Gly Ser Asn
             70                  75                  80 ttg gtg ctg ctg gca ggc agc ctg acc ctg ggc ctg gct ggt tcc ctg      346
Leu Val Leu Leu Ala Gly Ser Leu Thr Leu Gly Leu Ala Gly Ser Leu
         85                  90                  95 gcc tgg ctg gtc ctg ggc cgc gct gtg gtt ggc ttc gcc att tcc ctc      394
Ala Trp Leu Val Leu Gly Arg Ala Val Val Gly Phe Ala Ile Ser Leu
    100                 105                 110 tcc tcc atg gct tgc tgt atc tac gtg tca gag ctg gtg ggg cca cgg      442
Ser Ser Met Ala Cys Cys Ile Tyr Val Ser Glu Leu Val Gly Pro Arg
115                 120                 125                 130 cag cgg gga gtg ctg gtg tcc ctc tat gag gca ggc atc acc gtg ggc      490
Gln Arg Gly Val Leu Val Ser Leu Tyr Glu Ala Gly Ile Thr Val Gly
                135                 140                 145 atc ctg ctc tcc tat gcc ctc aac tat gca ctg gct ggt acc ccc tgg      538
Ile Leu Leu Ser Tyr Ala Leu Asn Tyr Ala Leu Ala Gly Thr Pro Trp
            150                 155                 160 gga tgg agg cac atg ttc ggc tgg gcc act gca cct gct gtc ctg caa      586
Gly Trp Arg His Met Phe Gly Trp Ala Thr Ala Pro Ala Val Leu Gln
            165                 170                 175 tcc ctc agc ctc ctc ttc ctc cct gct ggt aca gat gag act gca aca      634
Ser Leu Ser Leu Leu Phe Leu Pro Ala Gly Thr Asp Glu Thr Ala Thr
        180                 185                 190 cac aag gac ctc atc cca ctc cag gga ggt gag gcc ccc aag ctg ggc      682
His Lys Asp Leu Ile Pro Leu Gln Gly Gly Glu Ala Pro Lys Leu Gly
195                 200                 205                 210 ccg ggg agg cca cgg tac tcc ttt ctg gac ctc ttc agg gca cgc gat      730
Pro Gly Arg Pro Arg Tyr Ser Phe Leu Asp Leu Phe Arg Ala Arg Asp
                215                 220                 225 aac atg cga ggc cgg acc aca gtg ggc ctg ggg ctg gtg ctc ttc cag      778
Asn Met Arg Gly Arg Thr Thr Val Gly Leu Gly Leu Val Leu Phe Gln
            230                 235                 240 caa cta aca ggg cag ccc aac gtg ctg tgc tat gcc tcc acc atc ttc      826
Gln Leu Thr Gly Gln Pro Asn Val Leu Cys Tyr Ala Ser Thr Ile Phe
        245                 250                 255 agc tcc gtt ggt ttc cat ggg gga tcc tca gcc gtg ctg gcc tct gtg      874
Ser Ser Val Gly Phe His Gly Gly Ser Ser Ala Val Leu Ala Ser Val
    260                 265                 270 ggg ctt ggc gca gtg aag gtg gca gct acc ctg acc gcc atg ggg ctg      922
Gly Leu Gly Ala Val Lys Val Ala Ala Thr Leu Thr Ala Met Gly Leu
275                 280                 285                 290 gtg gac cgt gca ggc cgc agg gct ctg ttg cta gct ggc tgt gcc ctc      970
Val Asp Arg Ala Gly Arg Arg Ala Leu Leu Leu Ala Gly Cys Ala Leu
                295                 300                 305 atg gcc ctg tcc gtc agt ggc ata ggc ctc gtc agc ttt gcc gtg ccc     1018
Met Ala Leu Ser Val Ser Gly Ile Gly Leu Val Ser Phe Ala Val Pro
            310                 315                 320 atg gac tca ggc cca agc tgt ctg gct gtg ccc aat gcc acc ggg cag     1066
Met Asp Ser Gly Pro Ser Cys Leu Ala Val Pro Asn Ala Thr Gly Gln
        325                 330                 335
```

```
aca ggc ctc cct gga gac tct ggc ctg ctg cag gac tcc tct cta cct    1114
Thr Gly Leu Pro Gly Asp Ser Gly Leu Leu Gln Asp Ser Ser Leu Pro
    340                 345                 350 ccc att cca agg acc aat gag gac caa agg gag cca atc ttg tcc act    1162
Pro Ile Pro Arg Thr Asn Glu Asp Gln Arg Glu Pro Ile Leu Ser Thr
355                 360                 365                 370 gct aag aaa acc aag ccc cat ccc aga tct gga gac ccc tca gcc cct    1210
Ala Lys Lys Thr Lys Pro His Pro Arg Ser Gly Asp Pro Ser Ala Pro
                375                 380                 385 cct cgg ctg gcc ctg agc tct gcc ctc cct ggg ccc cct ctg ccc gct    1258
Pro Arg Leu Ala Leu Ser Ser Ala Leu Pro Gly Pro Pro Leu Pro Ala
            390                 395                 400 cgg ggg cat gca ctg ctg cgc tgg acc gca ctg ctg tgc ctg atg gtc    1306
Arg Gly His Ala Leu Leu Arg Trp Thr Ala Leu Leu Cys Leu Met Val
        405                 410                 415 ttt gtc agt gcc ttc tcc ttt ggg ttt ggg cca gtg acc tgg ctt gtc    1354
Phe Val Ser Ala Phe Ser Phe Gly Phe Gly Pro Val Thr Trp Leu Val
    420                 425                 430 ctc agc gag atc tac cct gtg gag ata cga gga aga gcc ttc gcc ttc    1402
Leu Ser Glu Ile Tyr Pro Val Glu Ile Arg Gly Arg Ala Phe Ala Phe
435                 440                 445                 450 tgc aac agc ttc aac tgg gcg gcc aac ctc ttc atc agc ctc tcc ttc    1450
Cys Asn Ser Phe Asn Trp Ala Ala Asn Leu Phe Ile Ser Leu Ser Phe
                455                 460                 465 ctc gat ctc att ggc acc atc ggc ttg tcc tgg acc ttc ctg ctc tac    1498
Leu Asp Leu Ile Gly Thr Ile Gly Leu Ser Trp Thr Phe Leu Leu Tyr
            470                 475                 480 gga ctg acc gct gtc ctc ggc ctg ggc ttc atc tat tta ttt gtt cct    1546
Gly Leu Thr Ala Val Leu Gly Leu Gly Phe Ile Tyr Leu Phe Val Pro
        485                 490                 495 gaa aca aaa ggc cag tcg ttg gca gag ata gac cag cag ttc cag aag    1594
Glu Thr Lys Gly Gln Ser Leu Ala Glu Ile Asp Gln Gln Phe Gln Lys
    500                 505                 510 aga cgg ttc acc ctg agc ttt ggc cac agg cag aac tcc act ggc atc    1642
Arg Arg Phe Thr Leu Ser Phe Gly His Arg Gln Asn Ser Thr Gly Ile
515                 520                 525                 530 ccg tac agc cgc atc gag atc tct gcg gcc tcc tga ggtcttttgg         1688
Pro Tyr Ser Arg Ile Glu Ile Ser Ala Ala Ser
                535                 540 gagtggcccc tgcccccaaa ggtggtctgc ttttgctggg gtaaaaagga tgaaagtctg    1748
agaatgccca actcttcatt ttgagtctca ggccctgaag gttcctgagg atctagcttc    1808
atgcctcagt ttccccattg acttgcacat ctctgcagta tttataagaa gaatattcta    1868
tgaagtcttt gttgcaccat ggacttttct caaagaatct caagggtacc aatcctggca    1928
ggaagtctct cccgatatca cccctaaatc caaatgagga tatcatcttt tctaatctct    1988
tttttcaact ggctgggaca ttttcggaag ggggaagtct ctttttttac tcttatcatt    2048
tttttttttt gaggtggagt ctcattctgt tgcccaggct ggcctgatct tggctcactg    2108
caacctccac ctcctgagtt caagcgattc ttgtgcctca gcctcctaag cagctgggac    2168
tacaggcgca tgcaaccata cccagctaat ttattttttag cagagatggg gtttcactgt    2228
gttggccagg ctggtcgtga actcctgagc tcaagtgatc cacccacctc agcctcccag    2288
agtgctagga ttacaggcct tttgactctt ttatctgagt tttattgacc cctctaattc    2348
tcttacccag aatatttatc cttcaccagc aactctgact cttttgacggg aggcctcagt    2408 tctagtcctt ggtctgctgg tgtcattgct gtaggaatga ccacgggcct cagtttcccc    2468
atttgtataa tgggaagcct gtaccaggtc attcttaaga tttctcctga ctccagtgag    2528
```

-continued

```
ctggaattct aaatgctggt ctaggagctg tctccaggat ggtgcaggat ggctttgcgg      2588
aaaggagatg ggtttggagg ccaacaaacc tgcttgtcaa tattgccttt gcctcttggc      2648
agcccttgaa cttgagtaaa taacaactcc ctgaacctca gtttcctcat ctgcagaatg      2708
gggataatta tgtcccaggg gtatatttag accctgtttc ctttcaggag ggtccccagc      2768
tggtccaggg cctgggaaat ttctacttat cctcattacc caggtccctc ctttggaccc      2828
tgtaaagggt cagggtgaat cagatggggg actgagcaag tagctatgac tgcagatcat      2888
gtaaggaagg gactgacaag aagctcccag atgctgggga gaatgaagag ctaaaataga      2948
tcctaggtgc tggatgcttt gtcatccatg cgtgcacata tgggtgctgg cagagccccc      3008
aaggactctg gcctctcgag ttctcctatc ttctccattc tagatgcttc ccttgtatcc      3068
agtgatgtgc tggagctggc tttgccaagc ttgtgagagc tggttgctac attttcagga      3128
tttttacaag ttggtaaaca cagccattat aaaaaattaa atgatttaaa tttataatta      3188
agtaaattac attaaaacaa aaaaattata ctcaaaattc attacttaat tttactacct      3248
gttactatta tctgtgcttt tgaggctatt tctacatagt aactcttatg gagacctagg      3308
ggagacaccg cgcatctctt cctgattccc cactcaatga catcatgtta gtctttggtt      3368
gcttaactgg ctgtggggag tgtttttgta tcacaaagat tagagaggac tacacatcag      3428
ggcttgattt attgtttgtt gattttctag acttcagaac atgctggata aaatgtcagt      3488
aatgcaaatt aaactttaaa gtatgtcttg tttgtagcca atacatggtg tatagcacca      3548
aaaaatggag ggattattct tccagtagtt gaacactgtc atccgtttca gctgacagct      3608
gctcaaatca tttaagaagg agttctgaca ttcattttca ttgttttact tttgtcttcc      3668
tcactagtgt aaacaaaaat ttcaaccagc attcatgccg aacctatacc cattcttcag      3728
tgcctagctg tacagttatc agggattttt atttgtagtc taattttgtc aaatcatggc      3788
caaatcgcag tgatagttga ctttggatac aaggtttggc aaaaaaaaaa atattaacaa      3848
aatattctgt aagaatcaat tgtctatatg gaatttagga taaagaatat ttacaataaa      3908
gaatatttac aataaagagt ttattattat ttgtaagttg tgtgcaacaa acatacccctt     3968 tatctctgta aaatttatac acacaaaaat taacaaaaga ttctgtaaga attaattggc      4028
tatatggaat ttaggataga atatttacaa taaagagtat ttacaat                   4075
```

<210> SEQ ID NO 2
<211> LENGTH: 541
<212> TYPE: PRT
<213> ORGANISM: Homo sapiens

<400> SEQUENCE: 2

```
Met Gly His Ser Pro Val Leu Pro Leu Cys Ala Ser Val Ser Leu
  1               5                  10                  15

Leu Gly Gly Leu Thr Phe Gly Tyr Glu Leu Ala Val Ile Ser Gly
                 20                  25                  30

Leu Leu Pro Leu Gln Leu Asp Phe Gly Leu Ser Cys Leu Glu Gln Glu
             35                  40                  45

Phe Leu Val Gly Ser Leu Leu Gly Ala Leu Leu Ala Ser Leu Val
         50                  55                  60

Gly Gly Phe Leu Ile Asp Cys Tyr Gly Arg Lys Gln Ala Ile Leu Gly
 65                  70                  75                  80

Ser Asn Leu Val Leu Leu Ala Gly Ser Leu Thr Leu Gly Leu Ala Gly
                 85                  90                  95
```

-continued

```
Ser Leu Ala Trp Leu Val Leu Gly Arg Ala Val Val Gly Phe Ala Ile
            100                 105                 110
Ser Leu Ser Ser Met Ala Cys Cys Ile Tyr Val Ser Glu Leu Val Gly
        115                 120                 125
Pro Arg Gln Arg Gly Val Leu Val Ser Leu Tyr Glu Ala Gly Ile Thr
    130                 135                 140
Val Gly Ile Leu Leu Ser Tyr Ala Leu Asn Tyr Ala Leu Ala Gly Thr
145                 150                 155                 160
Pro Trp Gly Trp Arg His Met Phe Gly Trp Ala Thr Ala Pro Ala Val
                165                 170                 175
Leu Gln Ser Leu Ser Leu Leu Phe Leu Pro Ala Gly Thr Asp Glu Thr
            180                 185                 190
Ala Thr His Lys Asp Leu Ile Pro Leu Gln Gly Gly Glu Ala Pro Lys
        195                 200                 205
Leu Gly Pro Gly Arg Pro Arg Tyr Ser Phe Leu Asp Leu Phe Arg Ala
    210                 215                 220
Arg Asp Asn Met Arg Gly Arg Thr Thr Val Gly Leu Gly Leu Val Leu
225                 230                 235                 240
Phe Gln Gln Leu Thr Gly Gln Pro Asn Val Leu Cys Tyr Ala Ser Thr
                245                 250                 255
Ile Phe Ser Ser Val Gly Phe His Gly Gly Ser Ser Ala Val Leu Ala
            260                 265                 270
Ser Val Gly Leu Gly Ala Val Lys Val Ala Ala Thr Leu Thr Ala Met
        275                 280                 285
Gly Leu Val Asp Arg Ala Gly Arg Arg Ala Leu Leu Leu Ala Gly Cys
    290                 295                 300
Ala Leu Met Ala Leu Ser Val Ser Gly Ile Gly Leu Val Ser Phe Ala
305                 310                 315                 320
Val Pro Met Asp Ser Gly Pro Ser Cys Leu Ala Val Pro Asn Ala Thr
                325                 330                 335
Gly Gln Thr Gly Leu Pro Gly Asp Ser Gly Leu Leu Gln Asp Ser Ser
            340                 345                 350
Leu Pro Pro Ile Pro Arg Thr Asn Glu Asp Gln Arg Glu Pro Ile Leu
        355                 360                 365
Ser Thr Ala Lys Lys Thr Lys Pro His Pro Arg Ser Gly Asp Pro Ser
    370                 375                 380
Ala Pro Pro Arg Leu Ala Leu Ser Ala Leu Pro Gly Pro Pro Leu
385                 390                 395                 400
Pro Ala Arg Gly His Ala Leu Leu Arg Trp Thr Ala Leu Leu Cys Leu
                405                 410                 415
Met Val Phe Val Ser Ala Phe Ser Phe Gly Phe Gly Pro Val Thr Trp
            420                 425                 430
Leu Val Leu Ser Glu Ile Tyr Pro Val Glu Ile Arg Gly Arg Ala Phe
        435                 440                 445
Ala Phe Cys Asn Ser Phe Asn Trp Ala Ala Asn Leu Phe Ile Ser Leu
    450                 455                 460
Ser Phe Leu Asp Leu Ile Gly Thr Ile Gly Leu Ser Trp Thr Phe Leu
465                 470                 475                 480
Leu Tyr Gly Leu Thr Ala Val Leu Gly Leu Gly Phe Ile Tyr Leu Phe
                485                 490                 495
Val Pro Glu Thr Lys Gly Gln Ser Leu Ala Glu Ile Asp Gln Gln Phe
            500                 505                 510
```

-continued

```
Gln Lys Arg Arg Phe Thr Leu Ser Phe Gly His Arg Gln Asn Ser Thr
            515                 520                 525

Gly Ile Pro Tyr Ser Arg Ile Glu Ile Ser Ala Ala Ser
    530                 535                 540

<210> SEQ ID NO 3
<211> LENGTH: 492
<212> TYPE: PRT
<213> ORGANISM: Homo sapiens

<400> SEQUENCE: 3

Met Glu Pro Ser Ser Lys Lys Leu Thr Gly Arg Leu Met Leu Ala Val
  1               5                  10                  15

Gly Gly Ala Val Leu Gly Ser Leu Gln Phe Gly Tyr Asn Thr Gly Val
             20                  25                  30

Ile Asn Ala Pro Gln Lys Val Ile Glu Glu Phe Tyr Asn Gln Thr Trp
         35                  40                  45

Val His Arg Tyr Gly Glu Ser Ile Leu Pro Thr Thr Leu Thr Thr Leu
     50                  55                  60

Trp Ser Leu Ser Val Ala Ile Phe Ser Val Gly Gly Met Ile Gly Ser
 65                  70                  75                  80

Phe Ser Val Gly Leu Phe Val Asn Arg Phe Gly Arg Arg Asn Ser Met
                 85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Phe Arg Gly Ala Leu Gly Thr Leu His
145                 150                 155                 160

Gln Leu Gly Ile Val Val Gly Ile Leu Ile Ala Gln Val Phe Gly Leu
                165                 170                 175

Asp Ser Ile Met Gly Asn Lys Asp Leu Trp Pro Leu Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220

Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
    290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
            340                 345                 350
```

-continued

```
Ile Ala Leu Ala Leu Leu Phe Gln Leu Pro Trp Met Ser Tyr Leu Ser
        355                 360                 365
Ile Val Ala Ile Phe Gly Phe Val Ala Phe Glu Val Gly Pro Gly
    370                 375                 380
Pro Ile Pro Trp Phe Ile Val Ala Glu Leu Phe Ser Gln Gly Pro Arg
385                 390                 395                 400
Pro Ala Ala Ile Ala Val Ala Gly Phe Ser Asn Trp Thr Ser Asn Phe
                405                 410                 415
Ile Val Gly Met Cys Phe Gln Tyr Val Glu Gln Leu Cys Gly Pro Tyr
                420                 425                 430
Val Phe Ile Ile Phe Thr Val Leu Leu Val Leu Phe Phe Ile Phe Thr
                435                 440                 445
Tyr Phe Lys Val Pro Glu Thr Lys Gly Arg Thr Phe Asp Glu Ile Ala
        450                 455                 460
Ser Gly Phe Arg Gln Gly Gly Ala Ser Gln Ser Asp Lys Thr Pro Glu
465                 470                 475                 480
Glu Leu Phe His Pro Leu Gly Ala Asp Ser Gln Val
                485                 490
```

<210> SEQ ID NO 4
<211> LENGTH: 1955
<212> TYPE: DNA
<213> ORGANISM: Homo sapiens

<400> SEQUENCE: 4

```
ctcaaaacat ggcagctcaa ttgcttcatc agagcaaaca agtgagagat ctcgaaactg      60
aacaacacag aaatcattta aacctaatc cgaaaatgac atccaccata tttgccgtct     120
tctattcatt agacgttgct aagtgatact tctagtgaca tctagaagag aagaggatgc     180
cactaggcca cgaataccag gagggtctca gtgtaatcag acttttata tgaaggctca     240
gggatccagg caccagtatt ccagtgaccc agcctcagaa gttacacagt gtcactctgc     300
aggctactga tcaaaccagt cacaagccca cttttatttc aagggaagga acaacgaatt     360
ctggagccat gttttcaaac tgccccagct attattattt tgaaactgt gcaaggatcc     420
cctggttcag aggtcttatg gatgctgtca tctttgctga gatacctgct tgtgccttca     480
gcatggaaga atgcctgtgt atccacctgt acggtagggg tcgctgtgac tttgactggt     540
gagggtacag ccactggtgc acatgcaaag gtgcctatct gtgaacacgt attgagaggc     600
tggataaggc tgcgcccatg tgagtgctgg gcttgtacgt gcattttgc ctgagtgagc     660
attagtggca gtgtccccag cctaccccct tcctgaatcc caggctcata gccaactgcc     720
cacctattc cacgtggatg cctgctgagc acctcaaatg tcacacagcc aagacagaac     780
tctggatctc cttcccagc cacaagctgc ccctcttcca gtctgtaagt tcttacggag     840
catatatatg tgatctgcct acttttctcc aacctcacca cagtgacatg agcccaaacc     900
aacttctcac cttgcaacag cctcccaggt gggaaggctg agtattctgg cccttaacca     960
gttagaactc cccagttatc tgtcctgctg atggggttga aatctacatt cctgaccctg    1020
gcccaccaaa gcccctccct tagctcccat ctccctcctc tctccctgtc ttctcctctg    1080
ctccagacac tctggcttca tttctgcgtt ttttgtaccc cataagctcc ttcccacccc    1140
ggggcctttg cctttgctgt tccccctgcg gggaatgccg gatctctgct cagatatcct    1200
cttctcagat cagcaagcta aagcagccac ctgtgtctgc ctaacccacc accgtagttt    1260
aactttctgc ctagtcttta tcactagctg atatttctca ggatccttta gttacttctt    1320
```

```
-continued tttcgtcttc ccctcctaga atgtaaactc ttcccctcct agaaggtaaa caaaagacct    1380
gttctgtttt gttcttcggc ccatcccaag cctagcgtag tgcctggtat gtggtggtgt    1440
ccaaacccaa gcgtggagtg aatgagggat gaatccatga gagagtgagc ggctccagtg    1500
ggtatgcgcg agtgtctcac tcggtgtaga tgtgtgtgtt gtgtgtgttg tgtgtgtgcg    1560
cacgctgggg aggccagaca agtgtggacc agtgattggg gcacctcttc cctgcaaaga    1620
ggccagggga agacagtgcg tgtggggtct tctaccaggg aggatggctt gctggtgtgt    1680 ccccccagg ggaggactac caacgaaggg gacccgggag atggcgggtg ggggcccccg     1740
ggaggacagt gggcgaggga gggggtcctt gccaggcctg gggcggccgg gggcggtcct    1800
gggctcccct ccgtcccgcc tccaggcctc ggggcctggc tggccgacgt ggcgttggcg    1860
gcgctgcgcg cgggagggca gggcaggagg gacagaggcg ggggcgggcc ggaaagtttg    1920
tccggcggca gcggcgttgg ggactccggc ggggg                              1955
```

ISOLATED NUCLEIC ACIDS AND POLYPEPTIDES ASSOCIATED WITH GLUCOSE HOMEOSTASIS DISORDERS AND METHOD OF DETECTING THE SAME

RELATED APPLICATIONS

This application is a continuation of PCT patent application No. PCT/US01/20167, filed Jun. 25, 2001, which claims priority to U.S. provisional patent application No. 60/215,477, filed Jun. 29, 2000, the disclosures of each of which are incorporated herein by reference in their entirety.

TECHNICAL FIELD

The present invention relates generally to nucleic acid sequences coding for sugar transporters useful for screening against glucose homeostasis disorders, and particularly to nucleic acid sequences coding for the glucose transporter which map to the region between D20S119 and D20S178 on human chromosome 20q13.

BACKGROUND ART

The publications and other materials used herein to illuminate the background of the invention, and in particular cases, to provide additional details respecting the practice, are incorporated herein by reference, and for convenience, are referenced by author and date in the text.

Diabetes mellitus is a condition in which the glucose homeostasis of a subject becomes unbalanced and leads to a hyperglycemic systemic condition. There are two forms of the diabetic condition, Type I and Type II. Type I diabetes usually occurs in individuals under approximately 20 years of age, is insulin-dependent, is commonly accompanied by ketoacidosis and represents about 10% of the diabetic population. Type II diabetes affects approximately 5 percent of the adult American population and represents about 90% of the diabetic population. Type II diabetes is commonly associated with obesity, usually occurs in individuals over approximately 40 years of age and is non-insulin dependent. A subset of type II diabetes can occur in younger individuals and is referred to as maturity onset diabetes of the young (MODY).

Interestingly, persons suffering from Type II diabetes can exhibit normal or even elevated levels of insulin, which helps the body maintain glucose homeostasis. This suggests that in Type II diabetes there might be a decreased sensitivity of the body to the effects of insulin, although defective insulin secretion can also be involved. Another critical factor in systemic maintenance of glucose homeostasis is the uptake of glucose by glucose transporter proteins. Furthermore, other factors include excessive hepatic glucose production and increased lipolysis in adipose tissue. See, e.g., Edelman, (1998) *Adv. Internal Med.* 43: 449-500; Vaag, (1999) *Dan. Med. Bull.* 46(3): 197-234.

Type II diabetes is typically slow to develop, is hereditary and is associated with obese individuals. Ongoing research has demonstrated that there is both a genetic component and an environmental component that leads to the Type II diabetic condition. The environmental component can lead to an acquired resistance to the action of insulin. The genetic component manifests itself as a condition rendering an individual predisposed to insulin resistance and more susceptible to the chronic onset of the diabetic condition. The genetic component can also involve glucose uptake by glucose transport proteins. Studies of the Pima Indian population, which has an unusually high incidence of Type II diabetes, and other populations, have indicated that alterations in glucose metabolism can be detected in subjects monitored before the onset of the condition. The genetic component presents a complex pattern of inheritance that is not fully understood.

Studies of the genetic component of the condition have indicated linkage of Type II diabetes susceptibility on many human chromosomes, including 2, 11, 12 and 20. A locus on chromosome 2 appears to be a major factor in development of Diabetes Mellitus in Mexican Americans (Hanis et al., (1996) *Nat. Genet.* 13: 161-66), a locus on chromosome 12 has been found in a Finnish populations (Mahtani et al., (1996) *Nat. Genet.* 14: 90-94) and a locus on chromosome 11q has been identified in Pima Indians (Hanson et al., (1998) *Diabetes* 46: 494-501). Studies by Zouali et al. suggest the location of a susceptibility locus on chromosome 20q in the PCK1 region. Zouali et al., (1997) *Hum. Mol. Genet.* 6:1401-08. At least three other studies present evidence for linkage of Type II diabetes on chromosome 20 in sibships. Ghosh et al., (1999) *Proc. Natl. Acad. Sci. USA* 96: 2198-2203; Bowden et al., (1997) *Diabetes* 46: 882-86; Ji et al., (1997) *Diabetes* 46: 876-81.

As noted, a hallmark of the Type II diabetic condition is a hyperglycemic imbalance in body glucose homeostasis. This condition can arise from a defect in the mechanism by which glucose is processed by the human body and can occur at various control points in the mechanism. A defect can occur, for example, during glucose uptake by the brain, glucose storage in the liver or insulin-dependent uptake in muscles and adipocytes in the human body.

Central to the uptake of glucose and the maintenance of glucose homeostasis are the glucose transporter proteins. These proteins control glucose absorption by the above-mentioned tissues. In mammalian cells, glucose transport is catalyzed by a number of membrane proteins, including the GLUT family of proteins, GLUT1-5, GLUT8, GLUTX1 and GLUT9. Glucose transport proteins are found in a wide variety of species, and share a common structural motif: glucose transport proteins are characterized by the presence of 12 connected transmembrane helical segments. See, e.g., Ibberson et al., (2000) *J. Biol. Chem.* 275: 4607-12; Doege et al., (2000) *J. Biol. Chem.* 275: 16275-80. An extracellular loop containing a glycosylation site is also present.

Although the precise primary defect in the Type II diabetic condition is presently unsettled, work in the field suggests that there is a strong causal link between the condition and glucose mobilization and metabolism. Zierler, (1999) *Am. J. Physiol.* 276(3, pt. 1): E409-26; Shepard and Kahn, (1999) *New Engl. J. Med.* 341(4): 248-57. Glucose transporter proteins are, therefore, likely candidates for analysis when attempting to explain the link between the Type II diabetic condition, as well as other glucose homeostatis imbalances, and their genetic components. Indeed, a mutation in GLUT4 has been found in a patient with Type II diabetes. Kusari, et al., (1991) *JCI* 88: 1323-30.

Clearly, it would be of tremendous value to researchers and clinicians to have a specific polynucleotide sequence coding for a glucose transport protein which is identified as being associated with human Type II diabetes. Such a result would permit diagnostic and therapeutic treatment of the condition, which if left untreated can lead to circulatory deficiencies and blindness. Traditional genetic approaches have proven to be inadequate to accomplish this goal. Linkage disequalibrium analysis, for example, which has historically proven helpful in studying complex disease genes, has not yet yielded results useful for Type II diabetes-related therapeutic treatments.

What is needed, therefore, is the identification of a polynucleotide sequence coding for a glucose transporter that is associated with human Type II diabetes and other glucose homeostasis disorders, as well as a method for accurately diagnosing a subject's susceptibility to, and the early detection of such conditions. Gene and drug therapy to relieve this condition, after the condition has manifested, is also needed. The present invention solves this problem by providing a polynucleotide and a polypeptide useful for diagnosing the susceptibility of a subject to human Type II diabetes and other glucose homeostasis disorders, a method for diagnosing the susceptibility of a subject to human Type II diabetes and other glucose homeostasis disorders using the polynucleotide and polypeptide and a method of treating the condition, all of which take into account the polymorphic nature of the polynucleotide sequence.

DISCLOSURE OF THE INVENTION

An isolated and substantially pure nucleic acid sequence located between D20S119 and D20S178 on human chromosome 20q13 is disclosed. The nucleic acid sequence comprises a nucleic acid sequence coding for a novel glucose transporting protein and having the sequence shown in SEQ ID NO: 1, or a nucleic acid sequence having at least 70% sequence identity with the nucleic acid sequence shown in SEQ ID NO: 1. Additionally, a nucleic acid sequence which hybridizes to and is at least 70% complementary to the glucose transporter-encoding nucleic acid sequence is disclosed.

Also disclosed is a method of facilitating a diagnosis of susceptibility to a glucose homeostasis disorder. The method comprises obtaining a biological sample from a subject; isolating a target nucleic acid sequence located between D20S119 and D20S178 on human chromosome 20q13, the target nucleic acid sequence encoding a glucose transporter polypeptide; sequencing the target nucleic acid sequence; and determining a sequence variation between a wild type nucleic acid sequence and the isolated target nucleic acid sequence, the presence of variations between the wild type nucleic acid sequence and the isolated target nucleic acid sequence indicating susceptibility in the subject to a disorder affecting glucose homeostasis.

A method of screening a biological sample for the presence of the novel glucose transporter polypeptide is also disclosed. The presence of polypeptide in the sample is detected by evaluating the formation and presence of antibody-polypeptide conjugates.

In another aspect, the present invention provides a method of screening a biological sample for the presence of antibodies immunoreactive with a novel glucose transporter polypeptide. In accordance with such a method, a biological sample is exposed to a glucose transporter polypeptide under biological conditions and for a period of time sufficient for antibody-polypeptide conjugate formation and the formed conjugates are detected.

A method of a facilitating a diagnosis of a disorder affecting glucose homeostasis is also disclosed. In one embodiment, the method comprises: (a) obtaining a biological sample from a subject; and (b) determining an amount of a glucose transporter polypeptide present in the biological sample, wherein the presence of a reduced amount of the glucose transporter polypeptide as compared to a standard facilitates a diagnosis of a disorder affecting glucose homeostasis. Optionally, the amount of glucose transporting protein in the biological sample can be determined by Western blot analysis.

In another embodiment, the method comprises: (a) obtaining a glucose transporter polypeptide from a subject; (b) determining an activity level of a glucose transporter polypeptide from the subject; and (c) detecting a variation in glucose transport activity between a wild type glucose transporter polypeptide and the glucose transporter polypeptide from the subject, wherein the presence of a glucose transport activity variation between the wild type glucose transporter polypeptide and the glucose transporter polypeptide from the subject facilitates a diagnosis of a disorder affecting glucose homeostasis.

The glucose transporter polypeptide can be obtained from a subject by isolating from the subject a biological sample comprising the glucose transporter polypeptide. In this case the method preferably further comprises determining the subcellular localization of the glucose transporter polypeptide in the biological sample.

In still a further embodiment, this invention pertains to therapeutic methods based upon the modulation of glucose transport via the polynucleotides and polypeptides described herein. Such therapeutic methods include gene therapy approaches using an isolated and purified polynucleotide of the present invention.

The foregoing aspects and embodiments have broad utility given the biological significance of glucose transport. By way of example, the foregoing aspects and embodiments are useful in the preparation of screening assays and assay kits that are used to identify compounds that affect or modulate glucose transport, or that are used to detect the presence of the proteins and nucleic acids of this invention in biological samples.

Accordingly, it is an object of the present invention to provide a novel glucose transporter polypeptide, and to provide a novel polynucleotide encoding the same. The object is achieved in whole or in part by the present invention. An object of the invention having been stated hereinabove, other objects will become evident as the description proceeds when taken in connection with the accompanying Figures and Laboratory Examples as best described herein below.

BRIEF DESCRIPTION OF THE DRAWINGS

FIG. 1A depicts a 5' region including the promoter region (SEQ ID NO: 4) of the glucose transporter-encoding polynucleotide sequence (SEQ ID NO: 1) found between D20S119 and D20S178 on human chromosome 20q13;

FIG. 1B depicts the cDNA polynucleotide sequence (SEQ ID NO: 1) of the glucose transporter found between D20S119 and D20S178 on human chromosome 20q13 and the corresponding deduced amino acid sequence (SEQ ID NO: 2);

FIG. 1C depicts the remaining 3' untranslated DNA sequence of the glucose transporter polynucleotide sequence (SEQ ID NO: 1) found between D2OS119 and D20S178 on human chromosome 20q13;

FIG. 5 is a diagram depicting an amino acid comparison of human glucose transporter 1 (GLUT1) (SEQ ID NO: 3) and the novel glucose transporter (SEQ ID NO: 2) of the present invention. Amino acids highlighted in bold are necessary for sugar transport function. This diagram also indicates the approximate regions of the transmembrane domains (TM).

DETAILED DESCRIPTION OF THE INVENTION

A. Definitions

Figure 2:
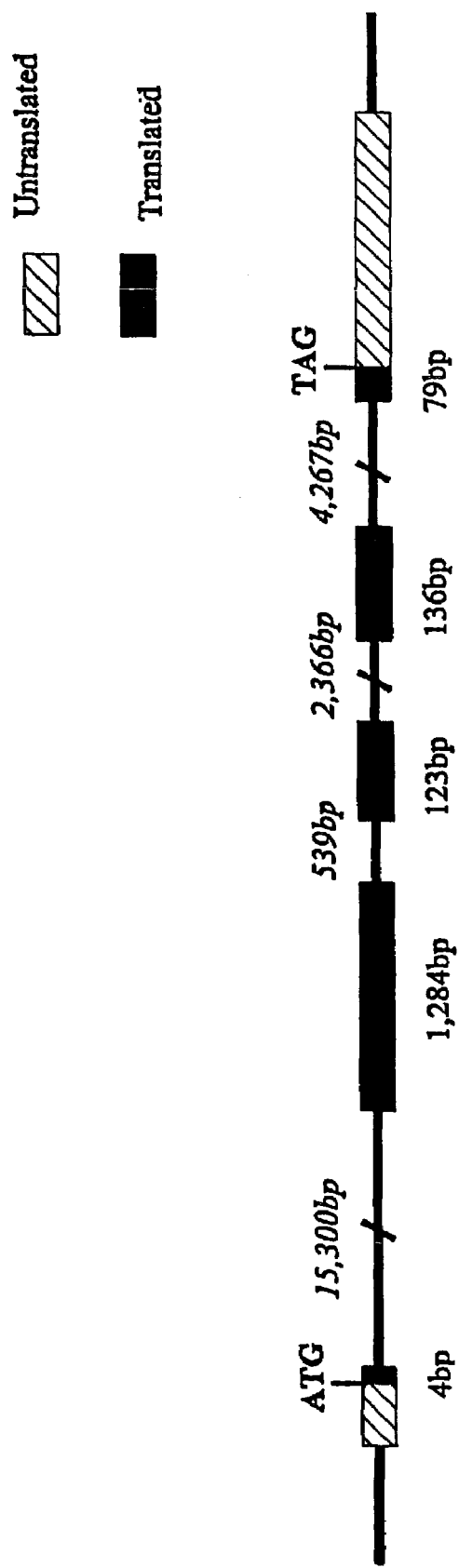
FIG. 2 is a schematic depicting the genomic structure and organization of the novel glucose transporter of the present invention.
Figure 3:
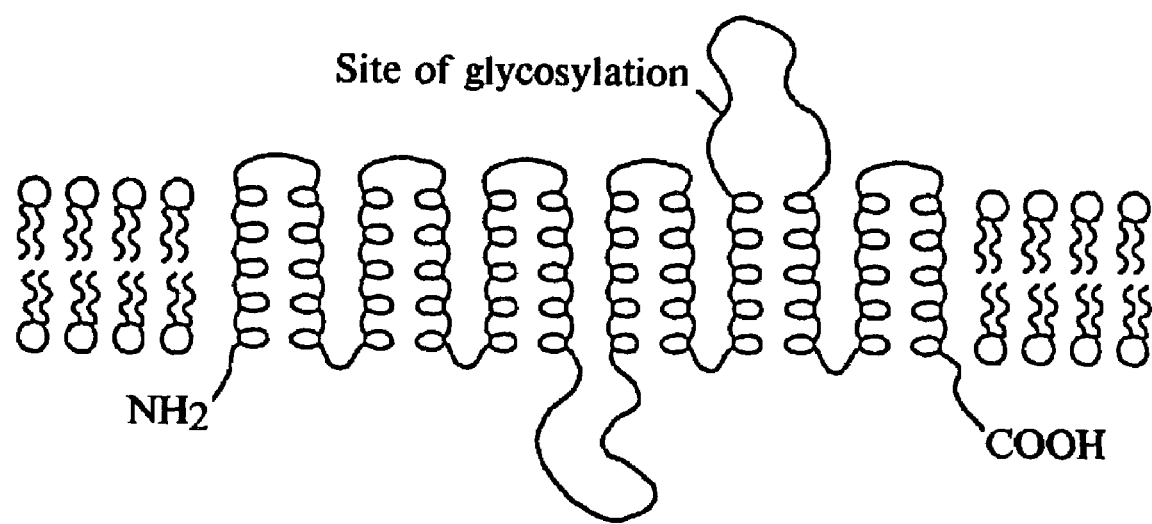
FIG. 3 is a schematic depicting the topology of the novel glucose transporter of the present invention.

Following long-standing patent law convention, the terms "a" and "an" mean "one or more" when used in this application, including the claims.

As used herein, the term "glucose transporter" carries the connotation generally recognized by those of skill in the art. The term therefore includes the ability of a protein to transport fructose, galactose and other sugars, as well as glucose.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "labeled" means the attachment of a moiety, capable of detection by spectroscopic, radiologic or other methods, to a probe molecule.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

As used herein, the term "polymorphism" refers to a difference in the nucleotide sequence of a given region as compared to a nucleotide sequence in a homologous region of another individual, in particular, a difference in the nucleotide sequence of a given region that differs between individuals of the same species. Polymorphisms include single nucleotide differences, differences in sequence of more than one nucleotide, insertions, inversions and deletions. The term refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus can be as small as one base pair.

As used herein, the term "transcription" means a cellular process involving the interaction of an RNA polymerase with a gene that directs the expression as RNA of the structural information present in the coding sequences of the gene. The process includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

As used herein, the term "expression" generally refers to the cellular processes by which a biologically active polypeptide is produced from RNA.

As used herein, the term "transcription factor" means a cytoplasmic or nuclear protein which binds to such gene, or binds to an RNA transcript of such gene, or binds to another protein which binds to such gene or such RNA transcript or another protein which in turn binds to such gene or such RNA transcript, so as to thereby modulate expression of the gene. Such modulation can additionally be achieved by other mechanisms; the essence of "transcription factor for a gene" is that the level of transcription of the gene is altered in some way.

As used herein, the term "susceptible to Type II diabetes" means a statistically significant increase in the probability of developing measurable symptoms and signs of Type II diabetes in an individual having a particular genetic mutation or polymorphism compared with the probability in an individual lacking the genetic mutation or polymorphism.

As used herein, the term "hybridization" means the binding of a probe molecule, a molecule to which a detectable moiety has been bound, to a target sample.

As used herein, the term "detecting" means confirming the presence of a target entity by observing the occurrence of a detectable signal, such as a radiologic or spectroscopic signal that will appear exclusively in the presence of the target entity.

As used herein, the term "sequencing" means the determining the ordered linear sequence of nucleic acids or amino acids of a DNA or protein target sample, using conventional manual or automated laboratory techniques.

As used herein, the term "isolated" means oligonucleotides substantially free of other nucleic acids, proteins, lipids, carbohydrates or other materials with which they can be associated, such association being either in cellular material or in a synthesis medium. The term can also be applied to polypeptides, in which case the polypeptide will be substantially free of nucleic acids, carbohydrates, lipids and other undesired polypeptides.

As used herein, the term "substantially pure" means that the polynucleotide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

As used herein, the term "parenteral" means intravenous, intra-muscular, intra-arterial injection, intraventricular, intrathecal or infusion introduction techniques.

As used herein, the term "primer" means a sequence comprising two or more deoxyribonucleotides or ribonucleotides, preferably more than three, and more preferably more than eight and most preferably at least about 20 nucleotides of an exonic or intronic region. Such oligonucleotides are preferably between ten and thirty bases in length.

As used herein, the term "DNA segment" means a DNA molecule that has been isolated free of total genomic DNA of a particular species. Furthermore, a DNA segment encoding a glucose transporter polypeptide refers to a DNA segment that contains SEQ ID NO: 1, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

As used herein, the phrase "enhancer-promoter" means a composite unit that contains both enhancer and promoter elements. An enhancer-promoter is operatively linked to a coding sequence that encodes at least one gene product.

As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

B. Polynucleotides and Polypeptides

In particular embodiments, the invention concerns isolated DNA segments and recombinant vectors incorporating DNA sequences which encode a glucose transporting polypeptide that includes within its amino acid sequence an amino acid sequence of the present invention. In other particular embodiments, the invention concerns recombinant vectors incorporating DNA segments that encode a polypeptide comprising the amino acid sequence of a human glucose transporting polypeptide; and these vectors also carry the promoter and enhancer regions associated with the nucleic acid sequence encoding the glucose transporting polypeptide.

B1. Polynucleotides

The present invention pertains to a previously unidentified gene located between markers D20S119 and D20S178 on chromosome 20q13. A Type II diabetes locus has previously been mapped to this region. The novel polynucleotide sequence, a preferred embodiment of which is shown in SEQ ID NO: 1, contains a 1626 bp coding sequence, and the full-length cDNA is 4.3 kb. The sequence is highly expressed in the liver and pancreas.

A preferred nucleic acid sequence of the present invention, such as that shown in SEQ ID NO: 1, is a glucose transporter sequence that is isolated from wild type cells. The sequence represents the glucose transporter nucleic acid sequence occurring in nature and existing without mutation. Therefore, wild type cells, as referred to herein, are those cells occurring in nature that contain non-mutated glucose transporter nucleic acid sequences. The wild type sequence is the native nucleic acid sequence and is the sequence against which assessments of polymorphism and mutation are made.

The terms "glucose transporter gene", "glucose transporter gene segment", "glucose transporter gene sequence", "glucose transporter polynucleotide", "glucose transporter nucleic acid molecule", and "glucose transporter nucleic acid sequence" refer to any nucleic acid sequence (e.g. a DNA sequence) that is substantially identical to a polynucleotide sequence encoding "glucose transporter gene product", "glucose transporter protein", "glucose transporter polypeptide", and "glucose transporter peptide" as defined below, and can also comprise any combination of associated control sequences. The terms also refer to RNA, or antisense sequences, complementary to such DNA sequences.

As used herein, the term "DNA segment" refers to a DNA molecule that has been isolated free of total genomic DNA of a particular species. Furthermore, a DNA segment encoding a glucose transporter polypeptide refers to a DNA segment that contains glucose transporter coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

B2. Polypeptides

A preferred deduced amino acid sequence of the polynucleotide sequence, SEQ ID NO: 2, is shown in FIG. 1. Analysis of the amino acid sequence revealed that a polypeptide comprising 541 residues. Analysis of the polypeptide shows that it contains 12 membrane-spanning helical sequences with a glycosylation site located on loop 9, which joins helices 9 and 10. This topology is typical of glucose transporting proteins. Mueckler, (1994) *Eur. J. Biochem.* 219: 713-25; Baldwin, (1993) *Biochim. Biophys. Acta* 1154: 17-49. The amino acid sequence also reveals several other motifs common to glucose transporters, including important amino acids essential to sugar transport function. Barrett et al., (1999) *Curr. Op. Cell Biol.* 11:496-502; Walmsley et al., (1998) *Trends Biochem. Sci.* 23:476-481. Representative amino acids implicated in sugar transport include but are not limited to those set forth in bold in FIG. 5.

The terms "glucose transporter gene product", "glucose transporter protein", "glucose transporter polypeptide", and "glucose transporter peptide" refer to peptides having amino acid sequences which are substantially identical to native amino acid sequences from the organism of interest and which are biologically active in that they comprise all or a part of the amino acid sequence of a glucose transporter polypeptide, or cross-react with antibodies raised against a glucose transporter polypeptide, or retain all or some of the biological activity of the native amino acid sequence or protein. Such biological activity can include immunogenicity.

The terms "glucose transporter gene product", "glucose transporter protein", "glucose transporter polypeptide", and "glucose transporter peptide" also include analogs of a glucose transporter polypeptide. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct glucose transporter analogs. There is no need for a "glucose transporter gene product", "glucose transporter protein", "glucose transporter polypeptide", and "glucose transporter peptide" to comprise all or substantially all of the amino acid sequence of a glucose transporter polypeptide gene product. Shorter or longer sequences are anticipated to be of use in the invention; shorter sequences are herein referred to as "segments". Thus, the terms "glucose transporter gene product", "glucose transporter protein", "glucose transporter polypeptide", and "glucose transporter peptide" also include fusion or recombinant glucose transporter polypeptides and proteins comprising sequences of the present invention. Methods of preparing such proteins are disclosed herein and are known in the art.

B3. Sequence Similarity and Identity

As used herein, the term "substantially similar" means that a particular sequence varies from nucleic acid sequence of SEQ ID NO: 1, or the amino acid sequence of SEQ ID NO: 2 by one or more deletions, substitutions, or additions, the net effect of which is to retain at least some of biological activity of the natural gene, gene product, or sequence. Such sequences include "mutant" or "polymorphic" sequences, or sequences in which the biological activity is altered to some degree but retains at least some of the original biological activity. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Additionally, nucleic acids that are substantially identical to SEQ ID NO: 1 and SEQ ID NO: 2, the preferred glucose transporter sequences, e.g. allelic variants, genetically altered versions of the gene, etc., bind to the provided glucose sequences under stringent hybridization conditions. By using probes, particularly labeled probes of DNA sequences, one can isolate homologous or related genes. The source of homologous genes can be any species, e.g. primate species; rodents, such as rats and mice, canines, felines, bovines, equines, yeast, nematodes, etc.

Between mammalian species, e.g. human and mouse, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nt long, more usually at least about 30 nt long, and can extend to the complete sequence that is being compared. Algorithms for sequence analysis are known in the art, such as BLAST, described in Altschul et al., (1990) *J. Mol. Biol.* 215: 403-10.

Percent identity or percent similarity of a DNA or peptide sequence can be determined, for example, by comparing sequence information using the GAP computer program, available from the University of Wisconsin Geneticist Computer Group. The GAP program utilizes the alignment method of Needleman et al., (1970) *J. Mol. Biol.* 48: 443, as revised by Smith et al., (1981) *Adv. Appl. Math.* 2:482. Briefly, the GAP program defines similarity as the number of aligned symbols (i.e., nucleotides or amino acids) which are similar, divided by the total number of symbols in the shorter of the two sequences. The preferred parameters for the GAP program are the default parameters, which do not impose a penalty for end gaps. See, e.g. Schwartz et al., eds., (1979), *Atlas of Protein Sequence and Structure, National Biomedical Research Foundation*, pp. 357-358; Gribskov et al., (1986) *Nucl. Acids. Res.* 14: 6745.

Thus, for sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman (1981) *Adv Appl Math* 2:482, by the homology alignment algorithm of Needleman & Wunsch (1970) *J Mol Biol* 48:443, by the search for similarity method of Pearson & Lipman (1988) *Proc Natl Acad Sci USA* 85:2444-2448, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel et al., 1992.

A preferred algorithm for determining percent sequence identity and sequence similarity is the BLAST algorithm, which is described in Altschul et al. (1990) *J Mol Biol* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff (1989) *Proc Natl Acad Sci USA* 89:10915.

In addition to calculating percent sequence identity, the BLAST algorithm also performs a statistical analysis of the similarity between two sequences. See, e.g., Karlin and Altschul (1993) *Proc Natl Acad Sci USA* 90:5873-5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The term "similarity" is contrasted with the term "identity". Similarity is defined as above; "identity", however, means a nucleic acid or amino acid sequence having the same amino acid at the same relative position in a given family member of a gene family. Homology and similarity are generally viewed as broader terms than the term identity. Biochemically similar amino acids, for example leucine and isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g. TCC to TCA, both of which encode serine.

As used herein, DNA analog sequences are "substantially identical" to specific DNA sequences disclosed herein if: (a) the DNA analog sequence is derived from coding regions of the nucleic acid sequence shown in SEQ ID NO: 1; or (b) the DNA analog sequence is capable of hybridization of DNA sequences of (a) under stringent conditions and which encode a biologically active gene product of the nucleic acid sequence shown in SEQ ID NO: 1; or (c) the DNA sequences are degenerate as a result of alternative genetic code to the DNA analog sequences defined in (a) and/or (b). Substantially identical analog proteins and nucleic acids will have between about 70% and 80%, preferably between about 81% to about 90% or even more preferably between about 91% and 99% sequence identity with the corresponding sequence of the native protein or nucleic acid. Sequences having lesser degrees of identity but comparable biological activity are considered to be equivalents.

As used herein, "stringent conditions" means conditions of high stringency, for example 6XSSC, 0.2% polyvinylpyrrolidone, 0.2% Ficoll, 0.2% bovine serum albumin, 0.1% sodium dodecyl sulfate, 100 μg/ml salmon sperm DNA and 15% formamide at 68° C. For the purposes of specifying additional conditions of high stringency, preferred conditions are salt concentration of about 200 mM and temperature of about 45° C. One example of such stringent conditions is hybridization at 4XSSC, at 65° C., followed by a washing in 0.1XSSC at 65° C. for one hour. Another exemplary stringent hybridization scheme uses 50% formamide, 4XSSC at 42° C.

In contrast, nucleic acids having sequence similarity are detected by hybridization under lower stringency conditions. Thus, sequence identity can be determined by hybridization under lower stringency conditions, for example, at 50° C. or higher and 0.1XSSC (9 mM NaCl/0.9 mM sodium citrate) and the sequences will remain bound when subjected to washing at 55° C. in 1XSSC.

As used herein, the term "complementary sequences" means nucleic acid sequences which are base-paired according to the standard Watson-Crick complementarity rules. The present invention also encompasses the use of nucleotide segments that are complementary to the sequences of the present invention. A particular example of a contemplated complementary nucleic acid segment is an antisense oligonucleotide.

Hybridization can also be used for assessing complementary sequences and/or isolating complementary nucleotide sequences. As discussed above, nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See, e.g., Wetmur & Davidson, (1968) *J. Mol. Biol.* 31: 349-70. Determining appropriate hybridization conditions to identify and/or isolate sequences containing high levels of homology is well known in the art. See, e.g., Sambrook et al., (1992), *Molecular Cloning: A Laboratory Manual*, Cold Spring Harbor, N.Y.

As used herein, the term "functionally equivalent codon" is used to refer to codons that encode the same amino acid, such as the ACG and AGU codons for serine. Glucose transporter encoding nucleic acid sequences having SEQ ID NO: 1 which have functionally equivalent codons are covered by the invention. Thus, when referring to the sequence examples presented in SEQ ID NO: 1, applicants contemplate substitution of functionally equivalent codons of Table 1 into the sequence examples of SEQ ID NO: 1. Thus, applicants are in possession of amino acid and nucleic acids sequences which include such substitutions but which are not set forth herein in their entirety for convenience.

TABLE 1

Functionally Equivalent Codons

| Amino Acids | | | Codons |
|---|---|---|---|
| Alanine | Ala | A | GGA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA GAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAG UAU |

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological protein activity where polypeptide expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

B4. Biological Equivalents

The present invention envisions and includes biological equivalents to the glucose transporter polypeptide of the present invention. The term "biological equivalent" refers to proteins having amino acid sequences which are substantially identical to the native amino acid sequences in the glucose transporter of the present invention and which are biologically active in that they are capable of mediating glucose uptake, or cross-reacting with anti-glucose transporter antibodies raised against a glucose transporter polypeptide of the present invention.

For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the invention is not limited to a particular mechanism of action. It is thus contemplated in accordance with the present invention that various changes can be made in the sequence of a glucose transporter polypeptide of the present invention or underlying nucleic acid sequence without appreciable loss of biological utility or activity.

Biologically equivalent peptides, as used herein, are peptides in which certain, but not most or all, of the amino acids can be substituted. Representative amino acids that are preferably not substituted include those implicated in glucose transport. Such amino acids are set forth in bold in FIG. 5. Thus, when referring to the sequence examples presented in SEQ ID NO: 1, applicants envision substitution of codons that encode biologically equivalent amino acids as described herein into the sequence example of SEQ ID NO: 1. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged, e.g. substitution of Ile for Leu. Changes designed by man can be introduced through the application of site-directed mutagenesis techniques, e.g., to introduce improvements to the antigenicity of the protein or to test a glucose transporter polypeptide of the present invention in order to glucose transport activity, or other activity at the molecular level.

Amino acid substitutions, such as those which might be employed in modifying a glucose transporter polypeptide of the present invention, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, (1982), incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.01); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that this invention is not limited to the particular nucleic acid and amino acid sequences of SEQ ID NOs: 1-2. Recombinant vectors and isolated DNA segments can therefore variously include the glucose transporter polypeptide-encoding region itself, include coding regions bearing selected alterations or modifications in the basic coding region, or include larger polypeptides which nevertheless comprise glucose transporter polypeptide-encoding regions or can encode biologically functional equivalent proteins or peptides which have variant amino acid sequences. Biological activity of a glucose transporter polypeptide can be determined, for example, by glucose uptake assays as disclosed herein.

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in SEQ ID NO: 1, such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also useful.

The DNA segments of the present invention encompass biologically functional equivalent glucose transporter polypeptides. Such sequences can rise as a consequence of codon redundancy and functional equivalency that are known to occur naturally within nucleic acid sequences and the proteins thus encoded. Alternatively, functionally equivalent proteins or peptides can be created via the application of recombinant DNA technology, in which changes in the protein structure can be engineered, based on considerations of the properties of the amino acids being exchanged. Changes can be introduced through the application of site-directed mutagenesis techniques, e.g., to introduce improvements to the antigenicity of the protein or to test glucose transporter mutants in order to examine activity in the modulation of calcium transport, or other activity at the molecular level. Site-directed mutagenesis techniques are known to those of skill in the art and are disclosed herein.

The invention further encompasses fusion proteins and peptides wherein the glucose transporter coding region is aligned within the same expression unit with other proteins or peptides having desired functions, such as for purification or immunodetection purposes.

Recombinant vectors form important further aspects of the present invention. Particularly useful vectors are those in which the coding portion of the DNA segment is positioned under the control of a promoter. The promoter can be that naturally associated with the glucose transporter gene, as can be obtained by isolating the 5' non-coding sequences located upstream of the coding segment or exon, for example, using recombinant cloning and/or PCR technology and/or other methods known in the art, in conjunction with the compositions disclosed herein.

In other embodiments, certain advantages will be gained by positioning the coding DNA segment under the control of a recombinant, or heterologous, promoter. As used herein, a recombinant or heterologous promoter is a promoter that is not normally associated with a glucose transporter gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al., 1992, specifically incorporated herein by reference). The promoters employed can be constitutive or inducible and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccinia virus promoter and the baculovirus promoter.

In an alternative embodiment, the present invention provides an expression vector comprising a polynucleotide that encodes a biologically active glucose transporter polypeptide in accordance with the present invention. Also preferably, an expression vector of the present invention comprises a polynucleotide that encodes a human glucose transporter polypeptide. More preferably, an expression vector of the present invention comprises a polynucleotide that encodes a polypeptide comprising an amino acid residue sequence of SEQ ID NO: 2. More preferably, an expression vector of the present invention comprises a polynucleotide comprising the nucleotide sequence of SEQ ID NO: 1. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a biologically active glucose transporter polypeptide in accordance with the present invention. SEQ ID NOs: 1-2 set forth nucleotide and amino acid sequences from a representative vertebrate, human. Also contemplated by the present invention are homologous or biologically functionally equivalent polynucleotides and glucose transporter polypeptide polypeptides found in other vertebrates, including particularly mouse and rat homologs. Preferably, a recombinant host cell of the present invention is transfected with the polynucleotide that encodes a human glucose transporter polypeptide. More preferably, a recombinant host cell of the present invention is transfected with the polynucleotide sequence set forth in SEQ ID NO: 1. Even more preferably, a recombinant host cell is a mammalian cell.

In another aspect, a recombinant host cell of the present invention is a prokaryotic host cell, including parasitic and bacterial cells. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the glucose transporter polypeptide in a manner to enable all necessary transcriptional and post-transcriptional modification.

In yet another embodiment, the present invention provides a method of preparing a glucose transporter polypeptide comprising transfecting a cell with polynucleotide that encodes a biologically active glucose transporter polypeptide in accordance with the present invention, to produce a transformed host cell, and maintaining the transformed host cell under biological conditions sufficient for expression of the polypeptide. The polypeptide can be isolated if desired, using any suitable technique. The host cell can be a prokaryotic or eukaryotic cell. Preferably, the prokaryotic cell is a bacterial cell of *Escherichia coli*. More preferably, a polynucleotide transfected into the transformed cell comprises the nucleotide base sequence of SEQ ID NO: 1. SEQ ID NOs: 1-2 set forth nucleotide and amino acid sequences for a representative vertebrate, human. Also provided by the present invention are homologs or biologically equivalent glucose transporter polynucleotides and polypeptides found in other vertebrates, particularly warm-blooded vertebrates, more particularly mammals, and even more particularly mouse and rat homologs.

As mentioned above, in connection with expression embodiments to prepare recombinant glucose transporter polypeptide proteins and peptides, it is contemplated that longer DNA segments will most often be used, with DNA segments encoding the entire glucose transporter polypeptide protein, functional domains or cleavage products thereof, being most preferred. However, it will be appreciated that the use of shorter DNA segments to direct the expression of glucose transporter polypeptides or core regions, such as can be used to generate anti-glucose transporter polypeptide antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins can have a minimum coding length on the order of about 4,000 or 5,000 nucleotides for a protein in accordance with SEQ ID NO: 1. DNA segments of the present invention can contain 300, 400, 500, 1,000, 1,500, 2,000, 2,500, 3,000, 3,500, 4,000, 4,500, or up to 5,000 nucleotides. Peptides of the present invention can contain 10, 20, 50, 100, 200, 300, 400, 500, 750, 1,000, or up to 1,500 amino acids.

B5. Sequence Modification Techniques

Modifications to the glucose transporter proteins and peptides described herein can be carried out using techniques known in the art, including site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants; for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., (1983) DNA 2:183; Sambrook et al., 1989) and can be achieved in a variety of ways generally known to those of skill in the art.

B6. Other Structural Equivalents

The knowledge of the structure of the glucose transporter polypeptide of the present invention provides a tool for investigating the mechanism of action of these proteins in a subject. For example, binding of these proteins to various substrate molecules can be predicted by various computer models. Upon discovering that such binding in fact takes place, knowledge of the protein structure then allows design and synthesis of small molecules which mimic the functional binding of the glucose transporter polypeptide to the substrate. This is the method of "rational" drug design, also described below.

Use of the isolated and purified glucose transporter polypeptide of the present invention in rational drug design is thus provided in accordance with the present invention. Additional rational drug design techniques are described in U.S. Pat. Nos. 5,834,228 and 5,872,011, herein incorporated in their entirety.

Thus, in addition to the peptidyl compounds described herein, the inventors also contemplate that other sterically similar compounds can be formulated to mimic the key portions of the peptide structure. Such compounds can be used in the same manner as the peptides of the invention and hence are also functional equivalents. The generation of a structural functional equivalent can be achieved by the techniques of modeling and chemical design known to those of skill in the art. It will be understood that all such sterically similar constructs fall within the scope of the present invention.

C. Introduction of The Novel Glucose Transporter Polypeptide Into an Expression System In accordance with the present invention, where the nucleic acid sequence shown in SEQ ID NO: 1 itself is employed to introduce the present glucose transporter translation product into a system for study, a convenient method of introduction will be through the use of a recombinant vector that incorporates the desired gene, together with its associated promoter and enhancer sequences. The preparation of recombinant vectors is well known to those of skill in the art and described in many references, such as, for example, Sambrook et al. (1992), incorporated herein in its entirety.

C1. Vector Construction

It is understood that the DNA coding sequences to be expressed, in this case those encoding the present glucose transporter gene product, are positioned in a vector adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One can also desire to incorporate into the transcriptional unit of the vector an appropriate polyadenylation site (e.g., 5'-AATAAA-3'), if one was not contained within the original inserted DNA. Typically, these poly-A addition sites are placed about 30 to 2000 nucleotides "downstream" of the coding sequence at a position prior to transcription termination.

While use of the control sequences of the present gene will be preferred, other control sequences can be employed, so long as they are compatible with the genotype of the cell being treated. Thus, one can mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, a nucleic acid sequence coding for a human glucose transporter, a vector construct that will deliver the gene to the affected cells is desired. Viral vectors can be used. These vectors will preferably be an adenoviral, a retroviral, a vaccinia viral vector, adeno-associated virus or Lentivirus; these vectors are preferred because they have been successfully used to deliver desired sequences to cells and tend to have a high infection efficiency. Suitable vector-glucose transporter gene constructs are adapted for administration as pharmaceutical compositions, as described herein below. Viral promoters can also be of use in vectors of the present invention, and are known in the art.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, including the promoter sequence shown in SEQ ID NO: 4, or fragment thereof, provided such control sequences are compatible with the host cell systems.

The origin of replication can be provided either by construction of the vector to include an exogenous origin, such as can be derived from SV40 or other viral source, or can be provided by the host cell chromosomal replication mechanism. If the vector is integrated into the host cell chromosome, the latter is often sufficient.

Where a glucose transporter gene itself is employed it will be most convenient to simply use the sequence shown in SEQ ID NO: 1 directly, and optionally, in conjunction with the promoter sequence shown in SEQ ID NO: 4. However, it is contemplated that certain regions of SEQ ID NO: 1 can be employed exclusively without employing the entire nucleic acid sequence itself. It is proposed that it will ultimately be preferable to employ the smallest region needed to modulate biological activity so that one is not introducing unnecessary DNA into cells which receive a glucose transporter gene construct.

D. Use of the Novel Polynucleotide Sequence in Predictive Diagnostic Screening In light of the fact that the present nucleic acid sequence maps to a locus on chromosome 20 known to be associated with Type II diabetes, the level of expression of the glucose transporter of the present invention can be used in the investigation of normal, experimentally perturbed or disease-state metabolism. For example, the effect of a treatment, e.g. the administration of a drug can be studied by its effect on expression of the glucose transporter of the present invention. This approach can be used to optimize or monitor treatment or to assist in the discovery or evaluation of new treatments. Such treatments can focus on interactions between the nucleic acid or amino acid sequences of the present invention.

Clearly, the novel polynucleotide sequence has a role in the diagnostic predictive screening of individuals susceptible to the Type II diabetic condition. The polynucleotide sequence, or regions thereof, unique to the present invention can be used as probes to determine the presence, absence or, since the invention accommodates the polymorphic nature of the sequence, mutations in the identified glucose transporter protein. The absence or mutation of the wild type sequence can alert researchers and clinicians to the fact that the subject can be abnormally susceptible to Type II diabetes.

D1. Preparation of Probes and Conditions for Hybridization

As set forth above, in certain aspects, DNA sequence information provided by the invention allows for the preparation of probes that specifically hybridize to encoding sequences of the present glucose transporter DNA sequence. In these aspects, probes of an appropriate length are prepared based on a consideration of the encoding sequence for a polypeptide of the present invention. The ability of such probes to specifically hybridize to other encoding sequences lends them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to or mimic at least a 14 to 40 or so long nucleotide stretch of a nucleic acid sequence of the present invention. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having complementary stretches of 14 to 20 nucleotides, or even longer where desired, such as 30, 40, 50, 60, 100, 200, 300, or 500 nucleotides or up to the full length of the present DNA sequence. Such fragments can be readily prepared by, for example, directly synthesizing the fragment by chemical synthesis, by application of nucleic acid amplification technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. Such conditions are particularly selective, and tolerate little, if any, mismatch between the probe and the template or target strand.

Of course, for some applications, less stringent hybridization conditions are typically needed to allow formation of the heteroduplex; one of ordinary skill in the art will know how to adjust the hybridization conditions for optimizing particular procedures. For example, it is generally appreciated that conditions can be rendered more stringent by the addition of increasing amounts of formamide, which serves to destabilize the hybrid duplex in the same manner as increased temperature. Thus, hybridization conditions can be readily manipulated by one of skill in the art using known methods to carry out the desired function or experiment, without undue experimentation.

D2. Screening Procedure

The predictive screening process is performed as follows. The sample of nucleic acid to be probed will be substantially pure and free of contaminants that could interfere with the screening process. Nucleic acid purification methods known in the art or commercially available can be employed to remove contaminants. A DNA or RNA molecule and particularly a DNA segment or polynucleotide can be used for hybridization to a DNA or RNA source or sample suspected of encoding the glucose transporter polypeptide of the present invention; such molecules are referred to as "probes," and such hybridization is "probing". Such probes can be made synthetically. Probes useful in the present invention can be designed with sequences complementary to the sequence shown in SEQ ID NO: 1. The probing is accomplished by contacting, or hybridizing, the oligonucleotide probe to a DNA source suspected of possessing the glucose transporter DNA sequence of the present invention. In some cases, the probes constitute only a single probe, and in others, the probes constitute a collection of probes based on a certain amino acid sequence or sequences of the polypeptide and account in their diversity for the redundancy inherent in the genetic code. Other molecules which are neither DNA nor RNA but are capable of hybridizing in a similar manner and which are designed structurally to mimic the DNA or RNA sequence of the claimed glucose transporter DNA sequence are also provided.

A suitable sample to examine is a sample that is capable of expressing a polypeptide of the present invention and can be a genomic library of a cell line of interest. Alternatively, a source of DNA or RNA can include total DNA or RNA from the blood of a patient or a cell line of interest. Once the hybridization process of the invention has identified a candidate DNA segment, a positive clone can be confirmed by further hybridization, restriction enzyme mapping, sequencing and/or expression and testing.

D3. Analysis of Sample Screening Data

Screening data obtained using the present invention can be compared to data obtained from the nucleic acid and polypeptide sequence of the present invention. For example, DNA sequence data obtained from a sample can be compared to the sequence shown in SEQ ID NO: 1. The comparison can be made using manual or automated methods, the practicality of which will be determined by the size and quality of obtained data. Variations and abnormalities in nucleic acid sequence when comparing the sample's sequence and the sequence shown in SEQ ID NO: 1 can predict the susceptibility of the subject supplying the sample to Type II diabetes. Variations in known glucose binding motifs, for example, can be implicated in an observed decreased biological ability to transport glucose. Sequence variations can also be predictive or indicative of improper protein folding, improper insertion of the translated protein within the membrane or a range of other structural defects manifested in an observed systemic condition.

Individuals at risk for a glucose-related disorder can also be identified by the possession of structural defects in the claimed glucose transporter gene. A nucleic acid sequence from a subject can be analyzed, using the claimed invention and methodology known to those skilled in the art, for gross chromosomal rearrangements such as deletions, insertions, translocations, frame shifts or point mutations, as described above. Gross rearrangements affecting the reading frame of the gene are also detectable and likely to alter biological glucose transport activity.

D4. Uses of the Invention Related to Diagnostic Screening

The described DNA molecules can be used in a number of techniques beyond that described above, including their use as: (1) diagnostic tools to detect normal and abnormal DNA sequences in DNA derived from patient's cells; (2) reagents for detecting and isolating other members of the polypeptide family and related polypeptides from a DNA library potentially containing such sequences; (3) primers for hybridizing to related sequences for the purpose of amplifying those sequences; (4) primers for altering native glucose transporter DNA sequences; as well as (5) other techniques which rely on the similarity of the sequences of interest to those of the sequences herein disclosed.

D5. Mapping

FIG. 2 shows a schematic of the genomic structure and organization of the novel glucose transporter nucleic acid sequence. The sequence contains five exons and four introns. Untranslated sequences are found abutting exon 1 and exon 5. FIG. 2 also characterizes the splice sites of the exon/intron junctions. The exons vary in size from 56 bp to greater than 2597 bp. Spliced out introns vary in size from 539 to 15300 bp. Only 4 bp of the 5' coding sequence are present in exon 1 and similarly, 79 bp of the 3' coding sequence are present in exon 5.

The present invention can be used by researchers in the field to screen clinical isolates, laboratory-generated clones or samples for the investigation of Type II diabetes-related conditions and will aid in genetic mapping studies. The nucleic acid sequence of the present invention is particularly useful when employed, either as shown in SEQ ID NO: 1 or as fragments thereof, as a probe in a screening process. In this role, the nucleic acid sequence of the present invention can accommodate naturally occurring or artificially-created polymorphisms within the sequence. Mutations in the claimed invention can be associated with an increased susceptibility to Type II diabetes. Exemplary uses of the sequence in laboratory studies are presented, said uses being implemented in conjunction with standard laboratory techniques familiar to one skilled in the art. The uses presented are non-exhaustive and variations will be apparent to those skilled in the art.

The nucleic acid sequence that encodes for the claimed glucose transporter can be used to generate hybridization probes that are useful for mapping naturally occurring genomic sequences and/or disease loci. The sequences can be mapped to a particular chromosome or to a specific region of the chromosome using well-known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) *Blood Rev.* 7: 127-134, and Trask, B. J. (1991) *Trends Genet.* 7: 149-154.

FISH (as described in Verma et al. (1988) *Human Chromosomes: A Manual of Basic Techniques*, Pergamon Press, New York, N.Y.) can be correlated with other physical chromosome mapping techniques and genetic map data. Examples of genetic map data can be found in the 1994 Genome Issue of *Science* (265:1981f). Correlation between the location of the gene encoding the claimed glucose transporter on a physical chromosomal map and a specific disease, or predisposition to a specific disease, can help delimit the region of DNA associated with that genetic disease. The nucleotide sequences of the claimed invention can be used to detect differences in gene sequences between normal, carrier, or affected individuals.

In situ hybridization of chromosomal preparations and physical mapping techniques such as linkage analysis using established chromosomal markers can be used for extending genetic maps. Often the placement of a gene on the chromosome of another mammalian species, such as mouse, reveals associated markers also found in other mammals, such as humans, even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, a glucose transporter polypeptide of the present invention to between D20S119 and D20S178, any sequences mapping to that area can represent associated or regulatory genes for further investigation. The nucleotide sequences of the present invention can thus also be used to detect differences in the chromosomal location due to translocation, inversion, etc. among normal, carrier, or affected individuals.

The mapping methods of the present invention also employ genomic clones of the exons of the claimed glucose transporter. Coding and genomic sequences for the claimed glucose transporter in human is set forth in SEQ ID NO: 1 and FIG. 1. Sequences from exon/intron junctions of the human glucose transporter of the present invention, are set forth in Table 2.

glucose transporter gene. Once genetic variants have been detected in specific patient populations, e.g. glucose transporter mutations in patients with Type II diabetes, the present invention provides assays to detect the mutation by methods such as allele-specific hybridization (Stoneking, et al. (1991) *Am. J. Hum. Genet* 48(2): 370-82), or restriction analysis of amplified genomic DNA containing the specific mutation. Again, these detection methods can be automated using existing technology (See e.g., Wang, et al. (1998) *Science* 280(5366): 1077-82). In the case of genetic disease or human phenotypes caused by repeat expansion (Lafreniere, et al. (1997) *Nat Genet* 15(3): 298-302; Timchenko and Caskey (1996) *FASEB J.* 10(14): 1589-97, the invention provides an assay based on PCR of genomic DNA with oligonucleotide primers flanking the involved repeat.

The provided nucleic acid molecules can be labeled according to any technique known in the art, such as with radiolabels, fluorescent labels, enzymatic labels, sequence tags, etc. Such molecules can be used as allele-specific oligonucleotide probes. Body samples can be tested to determine whether the nucleic acid sequence encoding the glucose transporter of the present invention contains a polymorphism. Suitable body samples for testing include those comprising DNA, RNA or protein obtained from biopsies, including liver and pancreatic tissue biopsies; or from blood, prenatal; or embryonic tissues, for example.

D6a. Primer Selection and Design

In one embodiment of the invention two pairs of isolated oligonucleotide primers are provided. These sets of primers are optionally derived from one of the glucose transporter exons shown in FIG. 2. The oligonucleotide primers are

TABLE 2

Sequence at Exon/Intron Junction

| Exon #: | Exon size | 5' Splice Donor | 3' Splice Acceptor | Intron size | Amino acid |
|---|---|---|---|---|---|
| 1 | >56 bp | ATG G | gtaagt........ttttttag GC CAC | 15,300 bp | Gly-2 |
| 2 | 1,284 bp | CCA G | gtaag..........ccctag TG ACC | 539 bp | Val-430 |
| 3 | 123 bp | ATT G | gtgagt.........tttccag GC ACC | 2,366 bp | Gly-471 |
| 4 | 136 bp | AGA CG | gtagg.........gacag G TTC | 4,267 bp | Arg-516 |
| 5 | >2,597 bp | | | | |

D6. Use of the Novel Nucleic Acid Sequence in Genetic Assays and Polymorphism Identification The present invention provides genetic assays based on the genomic sequence of the human glucose transporter gene of the present invention. The intronic sequence flanking the individual exons encoding the glucose transporter gene, which are described in Table 2, is employed in the design of oligonucleotide primers suitable for the mutation analysis of human genomic DNA. Thus, intronic primers can be used to screen for genetic variants by a number of PCR-based techniques, including single-strand conformation polymorphism (SSCP) analysis (Orita, et al. (1989) *Proc. Natl. Acad. Sci. USA* 86(8): 2766-70), SSCP/heteroduplex analysis, enzyme mismatch cleavage, and direct sequence analysis of amplified exons (Kestila, et al. (1998) *Mol. Cell* 1(4): 575-82; Yuan, et al. (1999) *Hum. Mutat.* 14(5): 440-6).

Automated methods can also be applied to the large-scale characterization of single nucleotide polymorphisms (Brookes (1999) *Gene* 234(2): 177-186; Wang, et al. (1998) *Science* 280(5366): 1077-82) within and near the human useful, for example, in detecting a polymorphism of the glucose transporter of the present invention. The primers direct amplification of a target polynucleotide prior to sequencing. In another embodiment of the invention isolated allele specific oligonucleotides (ASO) are provided. The allele specific oligonucleotides are also useful in detecting a polymorphism of the glucose transporter of the present invention.

The primers of the invention embrace oligonucleotides of sufficient length and appropriate sequence so as to provide initiation of polymerization on a significant number of nucleic acids in the polymorphic locus.

Environmental conditions conducive to synthesis include the presence of nucleotide triphosphates and an agent for polymerization, such as DNA polymerase, and a suitable temperature and pH. The primer is preferably single stranded for maximum efficiency in amplification, but can be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligqnucleotide primer typically contains 12-20 or more nucleotides, although it can contain fewer nucleotides. The primers should have sufficient complementarity with the 5' and 3' sequences flanking the transition to hybridize therewith and permit amplification of the genomic locus.

Oligonucleotide primers of the invention are employed in the amplification method, which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized (+) and (−) strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention can be prepared using any suitable method, such as conventional phosphotriester and phosphodiester methods or automated embodiments thereof. In one such automated embodiment, diethylphosphoramidites are used as starting materials and can be synthesized as described by Beaucage et al., (1981) *Tetrahedron Lett.* 22:1859-1862. One method for synthesizing oligonucleotides on a modified solid support is described in U.S. Pat. No. 4,458,066.

D6b. Amplification Techniques

Any nucleic acid specimen, in purified or non-purified form, can be utilized as the starting nucleic acid or acids, providing it contains, or is suspected of containing, a nucleic acid sequence containing the polymorphic locus. Thus, the method can amplify, for example, DNA or RNA, including messenger RNA, wherein DNA or RNA can be single stranded or double stranded. In the event that RNA is to be used as a template, enzymes, and/or conditions optimal for reverse transcribing the template to DNA would be utilized. In addition, a DNA-RNA hybrid that contains one strand of each can be utilized. A mixture of nucleic acids can also be employed, or the nucleic acids produced in a previous amplification reaction herein, using the same or different primers can be so utilized. The specific nucleic acid sequence to be amplified, i.e., the polymorphic locus, can be a fraction of a larger molecule or can be present initially as a discrete molecule, so that the specific sequence constitutes the entire nucleic acid. It is not necessary that the sequence to be amplified be present initially in a pure form; it can be a minor fraction of a complex mixture, such as contained in whole human DNA.

DNA utilized herein can be extracted from a body sample, such as blood, tissue material (e.g. liver or pancreatic tissue), and the like by a variety of techniques such as that described by Sambrook et al. in *Molecular Cloning: A Laboratory Manual*, Cold Spring Harbor, N.Y., (1992). If the extracted sample is impure, it can be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90-100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization can also be added together with the other reagents if it is heat stable. This synthesis (or amplification) reaction can occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization can be any compound or system that will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described herein and this hybrid is used in subsequent steps of the method. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. See McPherson et al., eds., (1992) *PCR. A Practical Approach*, ILR Press.

The amplification products can be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as dideoxy sequencing, PCR, oligomer restriction (Saiki et al., (1985), *Bio-Technol.* 3: 1008-12) allele-specific oligonucleotide (ASO) probe analysis (Conner et al., (1983), *Proc. Natl. Acad. Sci. U.S.A.* 80: 278), oligonucleotide ligation assays (OLAs) (Landgren et al., (1988) *Science* 241: 1007), and the like. Molecular techniques for DNA analysis have been reviewed (Landgren et. al., (1988), *Science* 242: 229-37.

D6c. Additional Amplification Methods

Preferably, the method of amplifying is by PCR, as described herein and in U.S. Pat. Nos. 4,683,195; 4,683,202; and 4,965,188; each of which is hereby incorporated by reference; and as is commonly used by those of ordinary skill in the art. Alternative methods of amplification have been described and can also be employed as long as the locus amplified by PCR using primers of the invention is similarly amplified by the alternative technique. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA.

Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to about $10^8$ copies within 60 to 90 minutes.

Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is about $10^8$ to about $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest.

Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair.

Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer.

SDA produces greater than about a $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification if the invention, these other methods can also be used to amplify any nucleic acid sequence of the present invention as described in the method of the invention. Thus, the term "amplification technique" as used herein and in the claims is meant to encompass all the foregoing methods.

D6d. Detection of Polymorphisms

In another embodiment of the present invention, a method is provided for identifying a subject having a polymorphism of a nucleic acid sequence encoding a glucose transporter polynucleotide of the present invention, comprising sequencing a target nucleic acid of a sample from a subject by dideoxy sequencing, preferably following amplification of the target nucleic acid.

In another embodiment of the present invention a method is provided for identifying a subject having a polymorphism of the nucleic acid sequence shown in SEQ ID NO: 1, comprising contacting a target nucleic acid of a sample from a subject with a reagent that detects the presence of a polymorphism in the nucleic acid sequence shown in SEQ ID NO: 1 and detecting the reagent. A number of hybridization methods are disclosed herein and are well known to those skilled in the art. Many of them are useful in carrying out the invention.

D6e. Hybridization Conditions and Detection

As discussed above, nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those of ordinary skill in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., (1968) Wetmur & Davidson, *J. Mol. Biol.* 31: 349-70).

Accordingly, a nucleotide sequence of the present invention can be used for its ability to selectively form duplex molecules with complementary stretches of the nucleic acid sequence shown in SEQ ID NO: 1. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M-0.15M salt at temperatures of about 50° C. to about 70° C. including particularly temperatures of about 55° C., about 60° C. and about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M-0.9M salt, at temperatures ranging from about 20° C. to about 55° C., including particularly temperatures of about 25° C., about 37° C., about 45° C., and about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate technique, such as a label, for determining hybridization. A wide variety of appropriate indicator reagents are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a reagent visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified via the label.

The materials for use in the method of the invention are ideally suited for the preparation of a screening kit. Such a kit can comprise a carrier having compartments to receive in close confinement one or more containers such as vials, tubes, and the like, each of the containers comprising one of the separate elements to be used in the method. For example, one of the containers can comprise an amplifying reagent for amplifying the DNA shown in SEQ ID NO: 1, such as the necessary enzyme(s) and oligonucleotide primers for amplifying target DNA from the subject.

Oligonucleotide primers comprising target flanking 5' and 3' polynucleotide sequence have substantially the sequence set forth in the flanking 5' and 3' portions of SEQ ID NO: 1 and Table 2, and sequences substantially complementary or homologous thereto. Other oligonucleotide primers for amplifying a target sequence will be known or readily ascertainable to those of skill in the art given the disclosure of the present invention presented herein.

E. Use of the Novel Polypeptide in Predictive Diagnostic Screening

The present invention provides a method of screening a biological sample for the presence of the novel glucose transporter polypeptide disclosed herein. In accordance with a screening assay method, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate). Additional details of methods for such assays are known in the art. The presence of polypeptide in the sample is detected by evaluating the formation and presence of antibody-polypeptide conjugates. Techniques for detecting such antibody-antigen conjugates or complexes are well known in the art and include but are not limited to centrifugation, affinity chromatography and the like, and binding of a secondary antibody to the antibody-candidate receptor complex.

In one embodiment, detection is accomplished by detecting an indicator affixed to the antibody. Exemplary and well-known indicators include radioactive labels (e.g., $^{32}P$, $^{125}I$, $^{14}C$), a second antibody or an enzyme such as horseradish peroxidase. Techniques for affixing indicators to antibodies are known in the art.

In another aspect, the present invention provides a method of screening a biological sample for the presence of antibodies immunoreactive with a novel glucose transporter polypeptide. Preferably, the antibody so identified has activity in the modulation of glucose transporter polypeptide biological activity in accordance with the present invention. In accordance with such a method, a biological sample is exposed to a glucose transporter polypeptide under biological conditions and for a period of time sufficient for antibody-polypeptide conjugate formation and the formed conjugates are detected.

A method of a facilitating a diagnosis of a disorder affecting glucose homeostasis is provided in accordance with the present invention. In one embodiment, the method comprises: (a) obtaining a biological sample from a subject; and (b) determining an amount of a glucose transporter polypeptide present in the biological sample, wherein the presence of a reduced amount of the glucose transporter polypeptide as compared to a standard facilitates a diagnosis of a disorder affecting glucose homeostasis. Optionally, the amount of glucose transporting protein in the biological sample can be determined by Western blot analysis.

In another embodiment, the method comprises: (a) obtaining a glucose transporter polypeptide from a subject; (b) determining an activity level of a glucose transporter polypeptide from the subject; and (c) detecting a variation in glucose transport activity between a wild type glucose transporter polypeptide and the glucose transporter polypeptide from the subject, the presence of a glucose transport activity variation between the wild type glucose transporter polypeptide and the glucose transporter polypeptide from the subject facilitating a diagnosis of a disorder affecting glucose homeostasis.

The glucose transporter polypeptide can be obtained from a subject by isolating from the subject a biological sample comprising the glucose transporter polypeptide. In this case the method preferably further comprises determining the subcellular localization of the glucose transporter polypeptide in the biological sample.

A biological sample to be screened can be a biological fluid such as extracellular or intracellular fluid (e.g. blood), or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

A preferred screening system to faciliate a diagnosis of a disorder affecting glucose homeostasis in a subject involves expression of a glucose transport polypeptide of the present invention from the subject in Xenopus oocytes (Gould and Lienhard (1989), *Biochem.* 28, 9447-57), followed by a glucose uptake assay. The Xenopus oocytes are transfected or microinjected with mRNA encoding the glucose transporter polypeptide of the present invention that has been isolated from a biological sample from the subject. This is another approach for obtaining the glucose transporter polypeptide from the subject.

The activity of a glucose transporter polypeptide present in the Xenopus oocytes is then determined by monitoring labeled glucose uptake. The glucose label can comprise any suitable label, but is preferably a radiolabel. Variations in glucose transport activity between a wild type glucose transporter polypeptide and the glucose transporter polypeptide from the subject are then detected. The presence of glucose transport activity variations between the wild type glucose transporter polypeptide and the isolated glucose transporter polypeptide facilitate the diagnosis of a disorder affecting glucose homeostasis in the subject.

Another preferred screening system to faciliate a diagnosis of a disorder affecting glucose homeostasis in a subject is a glucose uptake assay system. The rate of glucose uptake is monitored and variations from known parameters can indicate the presence of a glucose homeostatis disorder. Glucose uptake assays are also useful in monitoring cell culture glucose uptake in either transfected cells or in cells obtained from a patient, such as skin fibroblasts or lymphocytes, that comprise a glucose transporter polypeptide of the present invention. In addition, the subcellular localization of a glucose transporter polypeptide in a sample obtained from the subject is determined. The subcellular localization of the protein is determined because it has been shown that some glucose transporter polypeptides translocate between intracellular compartments and the plasma membrane in response to certain stimuli, such as insulin or exercise. Therefore, it is possible that a subject with a glucose transport disorder might localize the protein incorrectly within cells in the sample. An assessment of translocation can be made using standard immuocytochemical methodology well known to one of skill in the art, such as by immunofluorescent staining using an anti-glucose transporter polypeptide antibody.

F. Method of Screening for Chemical and Biological Modulators of the Biological Activity of the Glucose Transporter of the Present Invention A representative method of screening candidate substances for their ability to modulate the biological activity of the glucose transporter of the present invention comprises: (a) establishing replicate test and control samples that comprise a biologically active glucose transporter polypeptide; (b) administering a candidate substance to a test sample; (c) measuring the biological activity of the polypeptide in the test and the control samples; and (d) determining whether the candidate substance modulates biological activity relative to an appropriate control. By "modulate" is intended an increase, decrease, or other alteration of any or all biological activities or properties of the glucose transporter polypeptide. A representative polypeptide is disclosed in SEQ ID NO: 2.

A candidate substance identified according to the screening assay described herein has an ability to modulate the biological activity of a glucose transporter polypeptide. Such a candidate compound has utility in the treatment of disorders and conditions associated with the biological activity of a glucose transporter polypeptide. Candidate compounds can be hydrophobic, polycyclic, or both, molecules, and are typically about 500-1,000 daltons in molecular weight.

In a cell-free system, the method comprises the steps of establishing a control system comprising a glucose transporter polypeptide and a ligand to which the polypeptide is capable of binding; establishing a test system comprising a glucose transporter polypeptide, the ligand, and a candidate compound; and determining whether the candidate compound modulates the activity of the polypeptide by comparison of the test and control systems. A representative ligand comprises a monoclonal antibody, and in this embodiment, the biological activity or property screened includes binding affinity.

In another embodiment of the invention, the glucose transporter polypeptide or a catalytic or immunogenic fragment or oligopeptide thereof, can be used for screening libraries of compounds in any of a variety of drug screening techniques. The fragment employed in such screening can be free in solution, affixed to a solid support, borne on a cell surface, or located intracellularly. The formation of binding complexes, between the glucose transporter polypeptide and the agent being tested, can be measured. In a preferred embodiment, the glucose transporter polypeptide has an amino acid sequence of SEQ ID NO: 2. In a more preferred embodiment, the glucose transporter polypeptide is encoded by a polynucleotide of SEQ ID NO: 1.

Another technique for drug screening which can be used provides for high throughput screening of compounds having suitable binding affinity to the protein of interest as described in published PCT application WO 84/03564, herein incorporated by reference. In this method, as applied to a polypeptide of the present invention, large numbers of different small test compounds are synthesized on a solid substrate, such as plastic pins or some other surface. The test compounds are reacted with the polypeptide, or fragments thereof, and washed. Bound polypeptide is then detected by methods well known in the art. The purified polypeptide can also be coated directly onto plates for use in the aforementioned drug screening techniques. Alternatively, non-neutralizing antibodies can be used to capture the peptide and immobilize it on a solid support.

In one embodiment, a method of screening for a modulator of a glucose transport polypeptide encoded by a nucleic acid sequence located between D20S119 and D20S178 on human chromosome 20q13 comprises: providing cells from a cDNA expression library on a substrate, the cells comprising cDNA coding for the glucose transporter polypeptide; causing protein synthesis by the cells; subjecting the cells to a library of test samples; detecting an interaction between a test sample and a cell expressing the glucose transporter polypeptide; identifying a test sample that interacts with a cell expressing the glucose transporter polypeptide; and isolating the test sample that interacts with the glucose transporter polypeptide. In this method, cells can be derived from a prokaryote or a eukaryote, including *Homo sapiens*.

In another embodiment, a method of screening for a modulator of a glucose transport polypeptide encoded by a nucleic acid sequence located between D20S119 and D20S178 on human chromosome 20q13 comprises: affixing distinct colonies of cells from a cDNA expression library on a substrate, the cells comprising cDNA coding for the glucose transporter polypeptide; causing protein synthesis by said colonies on the substrate; subjecting the colonies of cells to a library of test samples; detecting an interaction between a test sample and a cell expressing the glucose transporter polypeptide; identifying a test sample that interacts with a cell expressing a glucose transporter polypeptide; and isolating a test sample that interacts with a glucose transporter polypeptide. In this method, the cells can also be derived from a prokaryote or a eukaryote, including *Homo sapiens*.

In yet another embodiment, a method of screening for a modulator of a glucose transport polypeptide encoded by a nucleic acid sequence located between D20S119 and D20S178 on human chromosome 20q13, comprises: providing a library of test samples; contacting a glucose transporter polypeptide with each test sample; detecting an interaction between a test sample and a glucose transporter polypeptide; identifying a test sample that interacts with a glucose transporter polypeptide; and isolating a test sample that interacts with a glucose transporter polypeptide.

In each of the foregoing embodiments, an interaction can be detected spectrophotometrically, radiologically or immunologically. An interaction between the glucose transporter polypeptide and a test sample can also be quantified. Such an interaction can be quantified by determining glucose transport activity.

A screening assay of the present invention can also involve determining the ability of a candidate substance to modulate, i.e. inhibit or promote glucose transporter biological activity and preferably, to thereby modulate the biological activity of the glucose transporter of the present invention in target cells. Target cells can be either naturally occurring cells known to contain the polypeptide gene product of the present invention or transformed cells produced in accordance with a process of transformation set forth herein above. The test samples can further comprise a cell or cell line that expresses the polypeptide gene product of the present invention, for example, Xenopus oocytes expressing a foreign glucose transporter as discussed above. The present invention also provides a recombinant cell line suitable for use in the exemplary method. Such cell lines can be mammalian, or human, or they can from another organism, including but not limited to yeast. Representative assays include genetic screening assays and molecular biology screens such as a yeast two-hybrid screen that will effectively identify genes related to a susceptibility to Type II diabetes and those genes important for proper glucose transport and other glucose transport-mediated cellular process. One version of the yeast two-hybrid system has been described (Chien et al., (1991), *Proc. Natl. Acad. Sci. USA,* 88: 9578-82) and is commercially available from Clontech (Palo Alto, Calif.).

As is well known in the art, a screening assay can provide a cell under conditions suitable for testing the modulation of the biological activity of a glucose transporter polypeptide. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. A glucose transporter pqlypeptide of the present invention can be expressed and utilized in a prokaryotic or eukaryotic cell. The host cell can also be fractionated into sub-cellular fractions where a structure of interest can be found. For example, cells expressing the polypeptide can be fractionated into the nuclei, the endoplasmic reticulum, vesicles, or the membrane surfaces of the cell.

F1. Rational Drug Design

A method of identifying modulators of the activity of the glucose transporter polypeptide of the present invention using rational drug design is provided in accordance with the present invention. The method comprises the steps of designing a potential modulator for the glucose transporter polypeptide of the present invention that will form non-covalent bonds with amino acids in the substrate binding site based upon the structure of the glucose transporter polypeptide of the present invention; synthesizing the modulator; and determining whether the potential modulator modulates the activity of the glucose transporter polypeptide of the present invention. Modulators can be synthesized using techniques known in the art.

The determination of whether the modulator modulates the biological activity of the glucose transporter polypeptide of the present invention is made in accordance with the screening methods disclosed herein, or by other screening methods known in the art. Preferably, the glucose transporter polypeptide comprises the amino acid sequence of SEQ ID NO: 2. More preferably, the glucose transporter polypeptide is encoded by a nucleic acid having the sequence of SEQ ID NO: 1.

F2. Method of Screening for Modulators of Levels and/or Activity of Glucose Transporter In accordance with the present invention there are also provided methods for screening candidate compounds for the ability to modulate in vivo glucose transporter levels and/or activity. Representative modulators of the level of the glucose transporter polypeptide of the present invention can comprise modulators of transcription or expression. Pharmaceuticals that increase or decrease the transcription or expression levels of the glucose transporter polypeptide of the present invention have important clinical application for the modulation of the biological activity of a glucose transporter polypeptide of the present invention. This modulation can affect glucose homeostasis. Preferably, the glucose transporter polypeptide comprises the amino acid sequence of SEQ ID NO: 2. More preferably, the glucose transporter polypeptide is encoded by a nucleic acid having the sequence of SEQ ID NO: 1.

The present invention thus includes a method for discovery of compounds that modulate the expression levels of the glucose transporter polypeptide of the present invention, and describes the use of such compounds. The general approach is to screen compound libraries for substances that increase or decrease the expression of the polypeptide.

In accordance with the present invention there is also provided a method of identifying a candidate compound or molecule that is capable of modulating the transcription level of the gene encoding the glucose transporter polypeptide of the present invention and thus is capable of acting as a therapeutic agent in the modulation of the effects of the polypeptide. This modulation can affect glucose homeostasis. Such modulation can be direct, i.e., through binding of a candidate molecule directly to the nucleotide sequence, whether DNA or RNA transcript, or such modulation can be achieved via one or more intermediaries, such as proteins other than the glucose transporter polypeptide of the present invention which are affected by the candidate compound and ultimately modulate transcription by any mechanism, including direct binding, phosphorylation or dephosphorylation, etc.

This method comprises contacting a cell or nucleic acid sample with a candidate compound or molecule to be tested. These samples contain nucleic acids which can contain elements that modulate transcription and/or translation of the nucleic acid sequence encoding a glucose transporter polypeptide (e.g. a nucleic acid sequence of SEQ ID NO: 1), such as an operatively linked promoter or putative upstream regulatory region (SEQ ID NO: 4), and a DNA sequence encoding a polypeptide that can be detected in some way. Thus, the polypeptide can be described as a "reporter" or "marker." Preferably, the candidate compound directly and specifically transcriptionally modulates expression of a nucleic acid sequence encoding the glucose transporter polypeptide of the present invention. Such compounds are anticipated to have therapeutic or pharmaceutical uses in treating glucose homeostasis-related diseases and/or disorders.

The DNA sequence is coupled to and under the control of the promoter, under conditions such that the candidate compound or molecule, if capable of acting as a transcriptional modulator of the nucleic acid sequence, causes a glucose transporter polypeptide of the present invention to be expressed and so produces a detectable signal, which can be assayed quantitatively and compared to an appropriate control. Candidate compounds or molecules of interest can include those which have the ability to increase or decrease, i.e., modulate, transcription from the promoter operatively linked to the nucleic acid sequence. The reporter gene can encode a reporter known in the art, such as luciferase.

In certain embodiments of the invention, the polypeptide so produced is capable of complexing with an antibody or is capable of complexing with biotin. In this case the resulting complexes can be detected by methods known in the art. The detectable signal of this assay can also be provided by messenger RNA produced by transcription of said reporter gene. Exactly how the signal is produced and detected can vary and is not the subject of the present invention; rather, the present invention provides a nucleic acid sequence for use in such an assay. The molecule to be tested in these methods can be a purified molecule, a homogenous sample, or a mixture of molecules or compounds. Further, in the method of the invention, the DNA in the cell can comprise more than one modulatable transcriptional regulatory sequence.

In accordance with the present invention there is also provided a rapid and high throughput screening method that relies on the methods described above. This screening method comprises separately contacting each of a plurality of substantially identical samples. In such a screening method the plurality of samples preferably comprises more than about $10^4$ samples, or more preferably comprises more than about $5 \times 10^4$ samples.

G. Therapeutic Applications

In accordance with the present invention, a variety of therapeutic applications are provided. The purified sequence can, for example, be used to alleviate or ameliorate the Type II diabetic condition using existing gene therapy techniques. Other applications provided by the present invention include drug therapy, wherein a compound is administered to a subject in order to affect the activity of the glucose transporter of the claimed invention. An additional therapy provided by the present invention includes the administration of the glucose transporter polypeptide of the present invention, or a biologically active fragment or analog thereof.

G1. Dosages of A Drug Modulating Glucose Transport Activity

As used herein, an "effective" dose refers to one that is administered in doses tailored to each individual patient manifesting symptoms of glucose transporter malfunction sufficient to cause an improvement therein. After review of the disclosure herein of the present invention, one of ordinary skill in the art can tailor the dosages to an individual patient, taking into account the particular formulation and method of administration to be used with the composition as well as patient height, weight, severity of symptoms, and stage of the disorder to be treated.

An effective dose and a therapeutically effective dose are generally synonymous. However, compounds can be administered to patients having reduced symptoms or even administered to patients as a preventative measure. Hence, the composition can be effective in therapeutic treatment even in the absence of symptoms of the disorder.

A unit dose can be administered, for example, 1 to 4 times per day. The dose depends on the route of administration and the formulation of a composition containing the compound or compounds. Further, it will be appreciated by one of ordinary skill in the art after receiving the disclosure of the present invention that it might be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques can vary with the patient and the severity of the disease. Particularly useful evaluative techniques include but are not limited to the glucose uptake assays disclosed herein.

G2. Methods of Transcriptionally Modulating in vivo Glucose Transporter Levels in the Treatment of Related Diseases and Disorders A method for transcriptionally modulating, in a multicellular organism, the expression of a gene encoding a glucose transporter in order to modulate glucose transporter biological activity in a warm-blooded vertebrate subject is also provided in accordance with the present invention. This method comprises administering to the warm-blooded vertebrate subject a compound at a concentration effective to transcriptionally modulate expression of glucose transporter or transporters.

In accordance with the present invention, the envisioned compound can optionally comprise an antibody or polypeptide prepared as described above and which transcriptionally modulates expression of glucose transporters. Optionally, the antibody or polypeptide directly binds to DNA or RNA, or directly binds to a protein involved in transcription.

Particularly envisioned chemical entities (e.g. small molecule mimetics) for use in accordance with the present invention do not naturally occur in any cell, whether of a multicellular or a unicellular organism. Even more particularly, the chemical entity is not a naturally occurring molecule, e.g. it is a chemically synthesized entity. Optionally, the compound can bind a modulatable transcription sequence of the gene. For example, the compound can bind a promoter region upstream of the claimed nucleic acid sequence encoding.

In the methods above, modulation of transcription results in either upregulation or downregulation of expression of the gene encoding the protein of interest, depending on the identity of the molecule that contacts the cell.

G2a. Gene Therapy

A nucleic acid sequence of the present invention, coding for glucose transporter, can be used for gene therapy in accordance with the present invention. The general strategy of gene therapy is the insertion and incorporation of an introduced non-native sequence of DNA into an organism's native DNA in order to facilitate a biological change. For example, the nucleic acid sequence shown in SEQ ID NO: 1 can be use to transform a cell and produce a cell in which a copy of the cell's defective genomic copy of a glucose transporting polypeptide-encoding nucleic acid sequence has been replaced by the transformed nucleic acid sequence. This approach can be used with cells capable of being grown in culture in order to study the function of the nucleic acid sequence. Representative gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, gene therapy directed toward modulation of glucose transporter activity, to thereby affect or modulate the biological activity of glucose transporter in a target cell is described. In one embodiment, a therapeutic method of the present invention provides a method for modulation of glucose transporter levels comprising: (a) delivering to the cell an effective amount of a DNA molecule comprising a polynucleotide that encodes a polypeptide that modulates the biological activity of one or more than one glucose transporter; and (b) maintaining the cell under conditions sufficient for expression of said polypeptide.

In a preferred embodiment, the delivered polypeptide comprises the sequence shown in SEQ ID NO: 2. Delivery can be accomplished by injecting the DNA molecule into the cell. Where the cell is in a subject, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. A representative transformed or transfected cell is a lymphocyte. Techniques for transforming or transfecting a cell with a DNA molecule of the present invention are set forth above.

Alternatively, the vehicle is a virus or an antibody that specifically infects a target cell or an antibody that immunoreacts with an antigen of a target cell. Retroviruses used to deliver the constructs to the host target tissues generally are viruses in which the 3'-LTR (linear transfer region) has been inactivated. That is, these are enhancerless 3'-LTR's, often referred to as SIN (self-inactivating viruses) because after productive infection into the host cell, the 3'-LTR is transferred to the 5'-end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell.

Antibodies have been used to target and deliver DNA molecules. An N-terminal modified poly-L-lysine (NPLL)-antibody conjugate readily forms a complex with plasmid DNA. A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

It is also envisioned that this embodiment of the present invention can be practiced using alternative viral or phage vectors, including retroviral vectors, adenoviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

By way of specific example, the human glucose transporter-encoding polynucleotide of the present invention, or a glucose transporter-encoding polynucleotide homolog from another warm-blooded vertebrate is introduced into isolated liver cells or other relevant cells. The re-injection of the transgene-carrying cells into the liver or other relevant tissues provides a treatment for susceptibility to impaired glucose transport function or other relevant diseases in human and animals.

G2a1. Gene Therapy Vector Construct Dosing

A nucleotide sequence of the present invention can be introduced into cells by introducing a virus containing a vector construct bearing the sequence of interest directly into a subject. This process requires the construction of a suitable vector. A suitable vector will contain the sequence of interest, as well as other functional sequences known to those skilled in the art to be required for viable transformation and transfection. A preferred procedure for alleviating a glucose transporter-related condition using a vector construct designed according to the described strategy is as follows.

The maximally tolerated dose (MTD) of vector construct when administered directly into the affected tissue is determined. Primary endpoints are: 1) the rate of transduction in abnormal and/or normal cells, 2) the presence and stability of this vector in the systemic circulation and in affected cells, and 3) the nature of the systemic (fever, myalgias) and local (infections, pain) toxicities induced by the vector. A secondary endpoint is the clinical efficacy of the vector construct.

For example, a 4 ml serum-free volume of viral (e.g. adenoviral, retroviral, etc.) vector construct (containing up to $5 \times 10^7$ viral particles in AIM V media) is administered daily per session. During each session, 1 ml of medium containing the appropriate titer of vector construct is injected into 4 regions of the affected tissue for a total of 4 ml per session in a clinical examination room. This is repeated daily for 4 days (4 sessions). This 16 ml total inoculum volume over 4 days is proportionally well below the one safely tolerated by nude mice (0.5 ml/20 g body weight).

Patient evaluation includes history and physical examination prior to initiation of therapy and daily during the 4-day period of vector construct injection. Toxicity grading is done using the ECOG Common Toxicity Criteria. CBC, SMA-20, urinalysis, and conventional studies are performed daily during this period. Evaluation will. include a regular determination of glucose transporter activity and an assessment of the progression, if any, of, for example, a Type II diabetic condition.

G2a2. Dose escalation and MTD

Patients are treated with $3 \times 10^6$ viral particles×4. Once they have all recovered from all grade 2 or less toxicities (except alopecia), and as long as grade 3-4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3 \times 10^6$ viral particles; 2) level 2, $1 \times 10^7$; 3) level 3, $3 \times 10^7$; 4)

level 4, 5×10$^7$. Patients with measurable disease are evaluated for a clinical response to vector construct. Histology and local symptoms are followed.

G2b. Antisense Oligonucleotide Therapy

In accordance with the present invention, expression of a glucose transporter can be modulated in a vertebrate subject through the administration of an antisense oligonucleotide derived from a nucleic acid molecule encoding the glucose transporter of the claimed invention. Therapeutic methods utilizing antisense oligonucleotides have been described in the art, for example, in U.S. Pat. Nos. 5,627,158 and 5,734,033, the contents of each of which are herein incorporated by reference.

Antisense oligodeoxynucleotides are short (usually about 30 bases) single-stranded synthetic DNAs having a nucleic acid sequence complementary to the target mRNA and the ability to form a hybrid duplex by hydrogen bonded base pairing. The formation of a hybrid duplex can prevent expression of the target mRNA code into its protein product and thus preclude subsequent deleterious effects of the polypeptide product. Because the mRNA sequence expressed by the gene is termed the sense sequence, the complementary sequence is termed the antisense sequence. Inhibition of MRNA is more efficient than inhibition of an enzyme's active site, since one mRNA molecule can give rise to multiple protein copies.

Synthetic oligodeoxynucleotides complementary to (antisense) mRNA of the c-myc oncogene have been used to specifically inhibit production of c-myc protein, thus arresting the growth of human leukemic cells in vitro, (See, e.g., Holt et al., (1988), *Mol. Cell Biol.* 8: 963-973; and Wickstrom et al., (1988) *Proc. Natl. Acad. Sci. USA*, 85: 1028-32). Oligodeoxynucleotides have also been employed as specific inhibitors of retroviruses, including the human immunodeficiency virus (HIV-I). (See, e.g., Zamencik and Stephenson, (1978) *Proc. Natl. Acad. Sci. USA*, 75: 280-84 and Zamencik et al., (1986) *Proc. Natl. Acad. Sci. USA*, 83: 4143-46).

Antisense nucleotide sequences can be introduced into a subject in a variety of ways, preferably by incubation of cells in the presence of the antisense nucleotide, more preferably through the use of liposomes and most preferably by in vitro or in vivo transfection of host cells by viruses.

G3. Formulation of Therapeutic Compositions

The glucose transporter biological activity modulating substances, gene therapy vectors, chemical agents and substances that inhibit or promote expression of the glucose transporter of the present invention are adapted for administration as a pharmaceutical composition as described herein. Additional formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

For the purposes described above, the identified substances can normally be administered systemically or partially, usually by oral or parenteral administration. The doses to be administered are determined depending upon age, body weight, symptom, the desired therapeutic effect, the route of administration, and the duration of the treatment, etc.; one of skill in the art of therapeutic treatment will recognize appropriate procedures and techniques for determining the appropriate dosage regimen for effective therapy. Various compositions and forms of administration are contemplated and are generally known in the art. Other compositions for administration include liquids for external use, and endermic linaments (ointment, etc.), suppositories and pessaries which comprise one or more of the active substance(s) and can be prepared by known methods.

Thus, the present invention provides pharmaceutical compositions comprising a polypeptide, polynucleotide, or molecule or compound of the present invention and a physiologically acceptable carrier. More preferably, a pharmaceutical composition comprises a compound discovered via the screening methods described herein.

A composition of the present invention is typically administered parenterally in dosage unit formulations containing standard, well-known nontoxic physiologically acceptable carriers, adjuvants, and vehicles as desired.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred technique of purifying the vector involves the use of buoyant density gradients, such as cesium chloride gradient centrifugation.

A transfected cell can also serve as a carrier of the therapeutic agent. By way of example, a liver cell can be removed from an organism, transfected with a polynucleotide of the present invention using methods set forth above and then the transfected cell returned to the organism (e.g. injected intra-vascularly).

The polypeptides, nucleic acid sequences, chemical agents and substances described above can further be administered to a mammal, particularly a human, using the methods described above. A sustained release formulation using a biodegradable polymer, micelles, gels, liposomes or transgenic technique is also provided in accordance with the present invention.

H. Generation of Genetically Modified Non-Human Species

The present invention contemplates the creation of transgenic non-human species expressing a glucose transporter of the present invention, including as a preferred embodiment, the nucleic acid sequence shown in SEQ ID NO: 1. Representative host species include rat and mouse. Mouse is especially preferred because a number of genetically modified mice already exist, e.g. the NOD mouse, the ob/ob mouse, the SCID mouse, etc. These modified mice are uniquely suited to the present invention because their genetic and corresponding expressed phenotypic traits add additional depth and dimension to the study of glucose homeostasis disorders.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. Nos. 5,573,933 (transgenic pigs); 5,162,215 (transgenic avian species) and U.S. Pat. No. 5,741,957 (transgenic bovine species), the entire contents of each of which are herein incorporated by reference.

Additionally, a nucleic acid sequence encoding the glucose transporter polypeptide of the present invention can be used to transform a cell. For example, a mutant form of the glucose transporter can be used to produce a cell in which a copy of the cell's genomic glucose transporter has been replaced by the transformed gene. This process can produce a cell which contains, for example, a modified or deleted for a copy of the gene. This approach can be used with cells capable of being grown in culture and in animals and is very useful when investigating the in vivo function and mechanism of the gene.

Thus, a genetically modified animal of the present invention can comprise a targeted modification of the glucose transporter gene. Animal strains with complete or partial functional inactivation of the present glucose transporter gene are generated using standard techniques of site-specific recombination in embryonic stem cells. Capecchi, M. R. (1989) *Science* 244(4910): 1288-92; Thomas, K. R., and Capecchi, M. R. (1990) *Nature* 346(6287):847-50; Delpire, E., et al. (1999) *Nat Genet* 22(2):192-5. Procedures analogous to those employed in the generation of a "knock-out" animal can be applied in the generation of a "knock-out" cell line.

Alternatives include the use of anti-sense or ribozyme glucose transporter constructs, driven by a universal or tissue-specific promoter, to reduce levels of the present glucose transporter, thus achieving a "knock-down" of the isoform (Luyckx, V. A., et al. (1999) *Proc. Natl. Acad. Sci. USA* 96(21): 12174-79). The invention also provides the generation of animal strains with conditional or inducible inactivation of individual or the glucose transporter gene (Sauer, B. (1998) *Methods* 14(4): 381-92; Ding, Y., et al. (1997) *J. Biol. Chem.* 272(44): 28142-48).

The present invention also provides animal strains with specific "knocked-in" modifications in the glucose transporter gene. This includes animals with genetically (Forlino, A., et al. (1999) *J. Biol. Chem.* 274(53): 37923-31) and functionally (Kissel, H., et al. (2000) *Embo. J.* 19(6): 1312-1326) relevant point mutations in the gene, in addition to manipulations such as the insertion of disease-specific repeat expansions (White, J. K., et al. (1997) *Nat Genet* 17(4):404-10).

I. Generation of Antibodies

In still another embodiment, the present invention provides an antibody immunoreactive with a polypeptide of the present invention. Preferably, an antibody of the invention is a monoclonal antibody. Techniques for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immmunizing an animal with an immunogen comprising a polypeptide or polynucleotide of the present invention, and collecting antisera from that immunized animal. A wide range of animal species can be used for the production of antisera. Because of the relatively large blood volume of rabbits, a rabbit is a preferred choice for production of polyclonal antibodies.

As is well known in the art, a given polypeptide or polynucleotide can vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Reagents for conjugating a polypeptide or a polynucleotide to a carrier protein are well known in the art and include glutaraldehyde, N-maleimidobencoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention provides a method of producing an antibody immunoreactive with the glucose transporter polypeptide, the method comprising: (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the glucose transporter polypeptide is capable of modulating calcium levels within or outside of cells in accordance with the present invention.

A monoclonal antibody of the present invention can be readily prepared through use of well-known techniques such as the hybridoma techniques exemplified in U.S. Pat. No 4,196,265 and the phage-displayed techniques disclosed in U.S. Pat. No. 5,260,203, the contents of which are herein incorporated by reference.

A typical technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1-200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the method of boosting and titering is repeated until a suitable titer is achieved. The spleen of the mouse with the highest titer is removed and the spleen lymphocytes are obtained by homogenizing the spleen with a syringe.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus "immortal". Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, and thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

J. Clinical Diagnosis of Type II Diabetes and Other Glucose Homeostasis-Related Imbalances The pattern of expression of one or a combination of glucose transporters can be used to diagnose persons at risk of diabetes or other glucose homeostasis disorders. This can be accomplished by monitoring the expression of the mRNA or the glucose transporter polypeptide of the present invention. As disclosed herein, the glucose transporter of the present invention maps to a locus on human chromosome 20 known to be associated with glucose homeostasis imbalances. Therefore, expression of this protein can be used to facilitate a diagnosis of the susceptibility and risk of an individual to Type II diabetes and other glucose homeostasis-related disorders.

The present invention, therefore, allows the identification of the presence or absence of a polymorphism in a human Type II diabetes gene and can therefore be used in the diagnosis of Type II diabetes or in the genetic counseling of individuals that have a family history of Type II diabetes, although the general population can also be screened. Such screening has the benefit of not only alerting an individual to his or her susceptibility to the Type II diabetic condition, but also allowing a practitioner to offer accurate advice regarding transmission of the condition to offspring. This early warning mechanism can provide invaluable assistance to susceptible offspring because it can allow him or her to prepare for the onset of the condition. It is possible that, with the knowledge of an individual's susceptibility to the condition, the individual can augment certain environmental factors to prevent or significantly delay the onset of the condition.

With further study centering around the present invention, the biological effects of a specific mutation are determined. Early detection and treatment of such a mutation can prevent later development of the condition. In addition, the financial costs difficulties associated with current treatments of glucose homeostasis-related disorders can be alleviated.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Example 1

Search of the EST Databases

The NCBI and TIGR expressed sequence tag (EST) databases were searched for novel isoforms of sugar transport proteins, using the polypeptide sequence of known sugar transporters, GLUTs 1-5. A BLAST-type search was performed, based on protein sequence motifs known to be present in the GLUT family of proteins. The search criteria included either the entire polypeptide sequence or keywords such as "sugar transporter". Candidate glucose transporter sequences were identified (e.g. a 306 base pair (bp) EST named EST183920 with locus and accession number AA313045) in the search and used in the generation of the full-length cDNA.

Laboratory Example 2

Generation of the Full-lencith cDNA and Chromosomal Localization

The 5' and 3' cDNA sequences were obtained using 5' and 3' rapid amplification of cDNA ends (RACE). The full-length cDNA was then amplified by long range PCR from normal human liver cDNA using the high fidelity Expand™ enzyme (Boehringer Mannheim, Mannheim, Germany).

The chromosomal localization and gene structure were determined by the identification of a BAC clone containing the genomic DNA sequence of the novel GLUT. The BAC clone was identified from the databases and had Locus number HS28H20 and accession number AL031055. It was 127,418 bp in length and had been localized to chromosome 20q13.1.

Laboratory Example 3

Tissue Distribution of the Novel Polynucleotide Sequence

Figure 4:
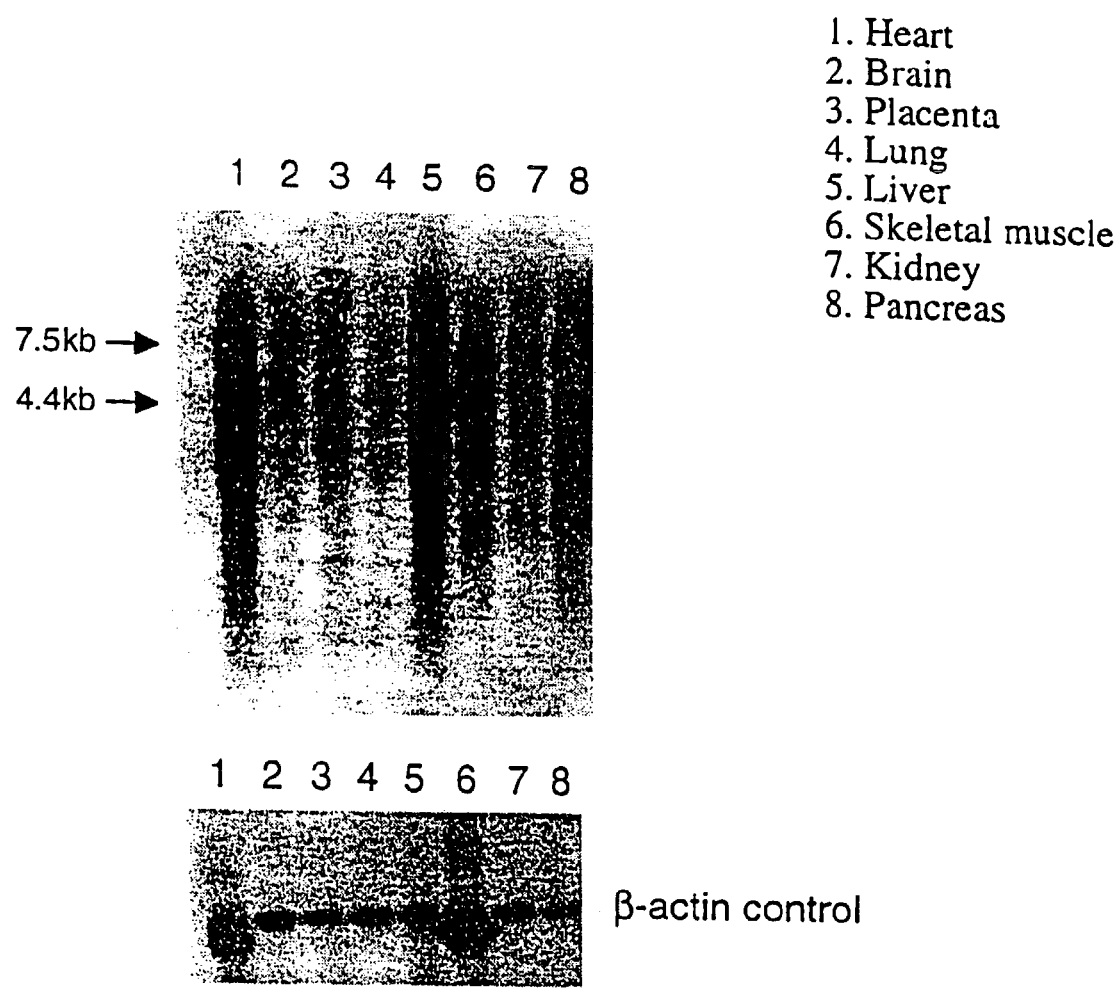
FIG. 4 is an autoradiograph of a Northern blot depicting the tissue distribution of the glucose transporter-encoding polynucleotide of the present invention.

FIG. 4 is an autoradiograph of a Northern blot showing the tissue distribution of the novel polynucleotide sequence. Heart, brain, placenta, lung, liver, skeletal muscle, kidney and pancreas tissue were probed for the presence of the novel sequence. Of the tissues probed, the sequence is most pronounced in liver and pancreas tissue.

Conditions for the Northern blot were as follows. The probe was a PCR product corresponding to residues 1394-1636 of SEQ ID NO: 1. The probe was labeled with $^{32}$P by the random priming method.

The Northern blot was bought commercially from Clontech of Palo Alto, Calif. Probe conditions were 68° C. hybridization for 1 hr using a hybridization buffer sold under the trademark EXPRESSHYB™ by Clontech of Palo Alto, Calif., followed by 2 washes with 2XSSC, 0.05% SDS for 40 minutes, each at room temperature.

Laboratory Example 4

Clinical Detection and Subsequent Isolation of the Nucleic Acid Sequence

A young male with histopathological and biochemical findings indicative of lysosomal glycogen storage disease with normal acid a-glucosidase (GAA) was studied. It was speculated that defective transport of glucose out of the lysosomes might be responsible. To investigate this, the coding region of GLUT4, a known muscle/adipose tissue glucose transporter, was isolated from a tissue sample taken from the patient. The nucleic acid sequence was sequenced and found to have no changes from wild type. This led to the consideration of the possible existence of an as yet undescribed glucose transporter.

A search of the EST databases using the amino acid sequences of the known GLUT isoforms, and subsequent cloning of the full-length cDNA, resulted in the identification of a novel glucose transporter protein. The identified isoform contains 541 amino acids, has a coding region of 1626 bp and it is highly expressed in the liver and pancreas. The polynucleotide and amino acid sequence are presented as SEQ ID NO: 1 and SEQ ID NO: 2 respectively.

The polypeptide gene product of the nucleic acid sequence shown in SEQ ID NO: 1 contains 12 transmembrane helices and contains several conserved motifs that are consistent with the protein's function as a sugar transporter. Mutation analysis indicated that this gene is not responsible for the lysosomal storage disease with normal GAA. This novel glucose transporter gene is located between D20S119 and D20S178 on chromosome 20q13, a region of a chromosome where a diabetes mellitus type II locus has been previously mapped. The function, tissue distribution and chromosome localization, indicated that this novel glucose transporter is a gene implicated in the pathogenesis of diabetes.

It will be understood that various details of the invention may be changed without departing from the scope of the invention. Furthermore, the foregoing description is for the purpose of illustration only, and not for the purpose of limitation—the invention being defined by the claims.

What is claimed is:

1. An isolated cDNA or RNA sequence encoding a glucose transporting protein comprising the polypeptide sequence of SEQ ID NO:2.

2. The isolated cDNA sequence of claim 1 comprising the nucleotide sequence of SEQ ID NO:1.

3. An isolated nucleic acid sequence that is at least 99% identical to the isolated cDNA or RNA sequence of claim 1.

4. A recombinant vector comprising the isolated cDNA sequence of claim 1 or the isolated nucleic acid sequence of claim 3.

5. The recombinant vector of claim 4, wherein said recombinant vector is a viral vector.

* * * * *